United States Patent [19]
Capon et al.

[11] Patent Number: 5,837,544
[45] Date of Patent: Nov. 17, 1998

[54] METHOD OF INDUCING A CELL TO PROLIFERATE USING A CHIMERIC RECEPTOR COMPRISING JANUS KINASE

[75] Inventors: Daniel J. Capon, Hillsborough; Huan Tian, Cupertino; Douglas H. Smith, Foster City; Genine A. Winslow, Hayward, all of Calif.; Miriam Siekevitz, New York, N.Y.

[73] Assignee: Cell Genesys, Inc., Foster City, Calif.

[21] Appl. No.: 485,293

[22] Filed: Jun. 7, 1995

Related U.S. Application Data

[63] Continuation of Ser. No. 382,846, Feb. 3, 1995.
[51] Int. Cl.$^6$ .................. C12N 5/10; C12N 1/38
[52] U.S. Cl. .................. 435/375; 435/325; 435/69.7; 435/376; 435/377
[58] Field of Search .................. 536/23.4; 435/69.7, 435/240.2, 320.1, 325, 375, 376, 377; 530/387.3

[56] References Cited

U.S. PATENT DOCUMENTS

| | | | |
|---|---|---|---|
| 5,359,046 | 10/1994 | Capon et al. | 536/23.4 |
| 5,470,730 | 11/1995 | Greenberg et al. | 435/172.3 |
| 5,504,000 | 4/1996 | Littman et al. | 435/194 |

FOREIGN PATENT DOCUMENTS

| | | |
|---|---|---|
| 0340793 | 8/1989 | European Pat. Off. . |
| WO9319163 | 3/1993 | WIPO . |
| WO9429438 | 12/1994 | WIPO . |

OTHER PUBLICATIONS

Nakamura et al. (1994) Nature 369: 330–333.
Miyazaki et al. (1994) Science 266: 1045–1047.
Heinzel et al., *Use of Simian Virus 40 replication to amplify Epstein–Barr virus shuttle vectors in human cells*, J.Virol. 63:3738–3746 (1988).
Kishimoto et al., *Cytokine Signal Transduction*, Cell 76:253–262 (1994).
Morgan and Anderson, *Human gene therapy*, Ann.Rev.Biochem. 62:191–217 (1993).
Mulligan, *The basic science of gene therapy*, Science 360:926–930 (1993).
Nienhuis et al., *Gene Transfer into Hematopoietic Stem Cells*, Cancer 67:2700–2704 (1991).
Orkin et al., Report and Recommendations of the Panel to Assess the NIH Investment in Gene Therapy, (1995).
Paul, *Tumor Immunology*, Fundamental Immunol., Chap. 34, pp. 923–955 (1989).
Riddell et al., *Genetically modified T–cell clones as a treatment for human viral diseases*, (Meeting Soc.Biol. .Therapy (Abstract), p. 50 (1993).
Sakai et al., *Signal transduction by a CD16/CD7/Jak2 fusion protein*, J.Biol.Chem. 270:18420–18427, (1995).
Spencer et al., *Controlling signal transduction with synthetic ligands.* Science 262:1019–1024 (1993).
Stancovski et al., *Targeting of T lymphocytes to Neu/HER–2–expressing cells using chimeric single chain Fv receptors*, J.Immunol. 151:6577–6582 (1993).
Travis, *Making molecular matches in the cell*, Science 262:989 (1993).
Weatherall, *Scope and limitations of gene therapy*, British Med.Bull. 51:1–11 (1995).

*Primary Examiner*—Stephen Walsh
*Assistant Examiner*—Michael D. Pak
*Attorney, Agent, or Firm*—Sughrue, Mion, Zinn, Macpeak & Seas, PLLC

[57] ABSTRACT

The present invention is directed to novel chimeric proliferation receptor proteins and DNA sequences encoding these proteins where the chimeric proteins are characterized in three general categories. In one category, the novel chimeric proteins comprise at least three domains, namely, an extracellular inducer-responsive clustering domain capable of binding an extracellular inducer that transmits a signal to a proliferation signaling domain, a transmembrane domain and a proliferation signaling domain that signals a host cell to divide. In the second category, the novel chimeric proteins comprise at least two domains, namely, an intracellular inducer-responsive clustering domain capable of binding an intracellular inducer and a proliferation signaling domain that signals the cell to divide. In yet a third category, a novel hybrid chimeric protein receptor is contemplated that contains an intracellular or extracellular inducer domain, a transmembrane domain, a proliferation signaling domain and an effector signaling domain in a single chain molecule. Whether the binding domain is intracellular or extracellular, the binding of inducer to these novel chimeric receptor proteins induces the clustering of the binding domains to each other and further signals the cell to proliferate, and optionally, signal an effector function. The present invention further relates to expression vectors containing the nucleic acids encoding the novel chimeric receptors, cells expressing the novel chimeric receptors and therapeutic methods of using cells expressing these novel receptors for the treatment of cancer, infectious disease and autoimmune diseases, for example.

5 Claims, 6 Drawing Sheets

OLIGO 1    CCTGCTGAACTTCACTCTGTCGACACAGAAGAAGATGCC

OLIGO 2    TCGACATGCAGTATCTAAATATAAAAGAGGACTGCAATGC

OLIGO 3    CATGGCATTGCAGTCCTCTTTTATATTTAGATACTGCATG

OLIGO 4    TATGTGTCAGTGGGGCGGGCC

OLIGO 5    CGCCCCACTGACACA

OLIGO 6    GTAAGGCAGGCCATTCCCATGTCGACACAGAAGAAGATGCC

OLIGO 7    TCTGTGTCGACATGGG

OLIGO 8    TCGACATGGCACCTCCAAGTGAGGAGACACCTCTGATCCCT-CAGC

OLIGO 9    GCTGAGGGATCAGAGGTGTCTCCTCACTTGGAGGTGCCATG

OLIGO 10   GATCCCTAGTTTATTCATGGGCC

OLIGO 11   CATGAATAAACTAGG

OLIGO 12   CATCCCCCAGTGGCGCAGAGGCATGTCGACAGAGTGAAGTTC

OLIGO 13   GTCGACATGCCTCTGC

OLIGO 14   GGGCCGCCGGAATTCCATGTCGACACAGAAGAAGATGCC

OLIGO 15   TCTGTGTCGACATGGA

OLIGO 16   CCTCAACAGGGTCCTTC

OLIGO 17   GCTGATCGTCGACAACTGCAGGAACACCGG

OLIGO 18   CATCTGTGATATCTCTACACCAAGTGAGTTG

OLIGO 19   GAAGAGCAAGCGCCATGTTGAAGCCATCATTACCATTCAC

FIG. 2A

OLIGO 20  AGCCTGAAACCTGAACCCCAATCCTCTGACAGAAGAACCC

OLIGO 21  CTGGCTGGTCGACGAACGGACGATGCCCCGCATTCCCACCC-
TGAAGAAC

OLIGO 22  GATTGGGGGATATCTCAGGTTTCAGGCTTTAG

OLIGO 23  GAAATCCCCTGGCTGTTAGTCGACGCGAGGGGGCAGGGCCTG

OLIGO 24  TGTTAGTCGACGCGAG

OLIGO 25  GGTCCACTCGAGATGGCCAGCAGCGGCATG

OLIGO 26  CCAGGTCCGATATCTTAGTCGACGTTCACCACGTCATAGTA

OLIGO 27  GACTGACTCTCGAGGGCGTGCAGGTGGAAACC

OLIGO 28  GACTGACTGTCGACTTCCAGTTTTAGAAGCTC

OLIGO 29  AATTCAAGGCCACAATGC

OLIGO 30  TCGAGCATTGTGGCCTTG

FIG. 2B

SEQUENCE LISTING ( 1 ) GENERAL INFORMATION:

( i i i ) NUMBER OF SEQUENCES: 31

( 2 ) INFORMATION FOR SEQ ID NO:1:

( i ) SEQUENCE CHARACTERISTICS:
( A ) LENGTH: 39 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:1:

CCTGCTGAAC TTCACTCTGT CGACACAGAA GAAGATGCC        3 9

( 2 ) INFORMATION FOR SEQ ID NO:2:

( i ) SEQUENCE CHARACTERISTICS:
( A ) LENGTH: 40 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:2:

TCGACATGCA GTATCTAAAT ATAAAGAGG ACTGCAATGC        4 0

( 2 ) INFORMATION FOR SEQ ID NO:3:

( i ) SEQUENCE CHARACTERISTICS:
( A ) LENGTH: 40 base pairs
( B ) TYPE: nucleic acid
( C ) STRANDEDNESS: single
( D ) TOPOLOGY: linear (  i  i  ) MOLECULE TYPE: DNA (genomic)

(  x  i  ) SEQUENCE DESCRIPTION: SEQ ID NO:3:

CATGGCATTG CAGTCCTCTT TTATATTTAG ATACTGCATG  40

( 2 ) INFORMATION FOR SEQ ID NO:4:

(  i  ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear (  i  i  ) MOLECULE TYPE: DNA (genomic)

(  x  i  ) SEQUENCE DESCRIPTION: SEQ ID NO:4:

TATGTGTCAG TGGGGCGGGC C  21

( 2 ) INFORMATION FOR SEQ ID NO:5:

(  i  ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear (  i  i  ) MOLECULE TYPE: DNA (genomic)

(  x  i  ) SEQUENCE DESCRIPTION: SEQ ID NO:5:

CGCCCCACTG ACACA  15

( 2 ) INFORMATION FOR SEQ ID NO:6:

(  i  ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: linear (  i  i  ) MOLECULE TYPE: DNA (genomic)

(  x  i  ) SEQUENCE DESCRIPTION: SEQ ID NO:6:

GTAAGGCAGG CCATTCCCAT GTCGACACAG AAGAAGATGC C  41

( 2 ) INFORMATION FOR SEQ ID NO:7:

(  i  ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear (  i  i  ) MOLECULE TYPE: DNA (genomic)

(  x  i  ) SEQUENCE DESCRIPTION: SEQ ID NO:7:

TCTGTGTCGA CATGGG  16

( 2 ) INFORMATION FOR SEQ ID NO:8:

(  i  ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear (  i  i  ) MOLECULE TYPE: DNA (genomic)

(  x  i  ) SEQUENCE DESCRIPTION: SEQ ID NO:8:

TCGACATGGC ACCTCCAAGT GAGGAGACAC CTCTGATCCC TCAGC  45

( 2 ) INFORMATION FOR SEQ ID NO:9:

( i ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:9:

GCTGAGGGAT CAGAGGTGTC TCCTCACTTG GAGGTGCCAT G  41

( 2 ) INFORMATION FOR SEQ ID NO:10:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:10:

GATCCCTAGT TTATTCATGG GCC  23

( 2 ) INFORMATION FOR SEQ ID NO:11:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:11:

CATGAATAAA CTAGG  15

( 2 ) INFORMATION FOR SEQ ID NO:12:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:12:

CATCCCCCAG TGGCGCAGAG GCATGTCGAC AGAGTGAAGT TC  42

( 2 ) INFORMATION FOR SEQ ID NO:13:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:13:

GTCGACATGC CTCTGC  16

( 2 ) INFORMATION FOR SEQ ID NO:14:

( i ) SEQUENCE CHARACTERISTICS:
   ( A ) LENGTH: 39 base pairs
   ( B ) TYPE: nucleic acid
   ( C ) STRANDEDNESS: single
   ( D ) TOPOLOGY: linear ( i i ) MOLECULE TYPE: DNA (genomic)

( x i ) SEQUENCE DESCRIPTION: SEQ ID NO:14:

GGGCCGCCGG AATTCCATGT CGACACAGAA GAAGATGCC                                   39

( 2 ) INFORMATION FOR SEQ ID NO:15:

( i ) SEQUENCE CHARACTERISTICS:
      ( A ) LENGTH: 16 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:15:

TCTGTGTCGA CATGGA                                                             16

( 2 ) INFORMATION FOR SEQ ID NO:16:

( i ) SEQUENCE CHARACTERISTICS:
      ( A ) LENGTH: 17 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:16:

CCTCAACAGG GTCCTTC                                                            17

( 2 ) INFORMATION FOR SEQ ID NO:17:

( i ) SEQUENCE CHARACTERISTICS:
      ( A ) LENGTH: 30 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:17:

GCTGATCGTC GACAACTGCA GGAACACCGG                                              30

( 2 ) INFORMATION FOR SEQ ID NO:18:

( i ) SEQUENCE CHARACTERISTICS:
      ( A ) LENGTH: 31 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:18:

CATCTGTGAT ATCTCTACAC CAAGTGAGTT G                                            31

( 2 ) INFORMATION FOR SEQ ID NO:19:

( i ) SEQUENCE CHARACTERISTICS:
      ( A ) LENGTH: 40 base pairs
      ( B ) TYPE: nucleic acid
      ( C ) STRANDEDNESS: single
      ( D ) TOPOLOGY: linear (i i) MOLECULE TYPE: DNA (genomic)

(x i) SEQUENCE DESCRIPTION: SEQ ID NO:19:

GAAGAGCAAG CGCCATGTTG AAGCCATCAT TACCATTCAC 40

(2) INFORMATION FOR SEQ ID NO:20:

(i) SEQUENCE CHARACTERISTICS:
      (A) LENGTH: 40 base pairs
      (B) TYPE: nucleic acid
      (C) STRANDEDNESS: single
      (D) TOPOLOGY: linear (i i) MOLECULE TYPE: DNA (genomic)

(x i) SEQUENCE DESCRIPTION: SEQ ID NO:20:

AGCCTGAAAC CTGAACCCCA ATCCTCTGAC AGAAGAACCC 40

(2) INFORMATION FOR SEQ ID NO:21:

(i) SEQUENCE CHARACTERISTICS:
      (A) LENGTH: 49 base pairs
      (B) TYPE: nucleic acid
      (C) STRANDEDNESS: single
      (D) TOPOLOGY: linear (i i) MOLECULE TYPE: DNA (genomic)

(x i) SEQUENCE DESCRIPTION: SEQ ID NO:21:

CTGGCTGGTC GACGAACGGA CGATGCCCCG CATTCCCACC CTGAAGAAC 49

(2) INFORMATION FOR SEQ ID NO:22:

(i) SEQUENCE CHARACTERISTICS:
      (A) LENGTH: 32 base pairs
      (B) TYPE: nucleic acid
      (C) STRANDEDNESS: single
      (D) TOPOLOGY: linear (i i) MOLECULE TYPE: DNA (genomic)

(x i) SEQUENCE DESCRIPTION: SEQ ID NO:22:

GATTGGGGGA TATCTCAGGT TTCAGGCTTT AG 32

(2) INFORMATION FOR SEQ ID NO:23:

(i) SEQUENCE CHARACTERISTICS:
      (A) LENGTH: 42 base pairs
      (B) TYPE: nucleic acid
      (C) STRANDEDNESS: single
      (D) TOPOLOGY: linear (i i) MOLECULE TYPE: DNA (genomic)

(x i) SEQUENCE DESCRIPTION: SEQ ID NO:23:

GAAATCCCCT GGCTGTTAGT CGACGCGAGG GGGCAGGGCC TG 42

(2) INFORMATION FOR SEQ ID NO:24:

(i) SEQUENCE CHARACTERISTICS:
      (A) LENGTH: 16 base pairs
      (B) TYPE: nucleic acid
      (C) STRANDEDNESS: single
      (D) TOPOLOGY: linear (i i) MOLECULE TYPE: DNA (genomic)

(x i) SEQUENCE DESCRIPTION: SEQ ID NO:24:

TGTTAGTCGA CGCGAG 16

( 2 ) INFORMATION FOR SEQ ID NO:25:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:25:

GGTCCACTCG AGATGGCCAG CAGCGGCATG 30

( 2 ) INFORMATION FOR SEQ ID NO:26:

( i ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:26:

CCAGGTCCGA TATCTTAGTC GACGTTCACC ACGTCATAGT A 41

( 2 ) INFORMATION FOR SEQ ID NO:27:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:27:

GACTGACTCT CGAGGGCGTG CAGGTGGAAA CC 32

( 2 ) INFORMATION FOR SEQ ID NO:28:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:28:

GACTGACTGT CGACTTCCAG TTTTAGAAGC TC 32

( 2 ) INFORMATION FOR SEQ ID NO:29:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:29:

AATTCAAGGC CACAATGC 18

( 2 ) INFORMATION FOR SEQ ID NO:30:

(i) SEQUENCE CHARACTERISTICS:
    (A) LENGTH: 18 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:30:

TCGAGCATTG TGGCCTTG                                                    18

(2) INFORMATION FOR SEQ ID NO:31:

(i) SEQUENCE CHARACTERISTICS:
    (A) LENGTH: 14 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:31:

Gly Ser Thr Ser Gly Ser Gly Lys Ser Ser Glu Gly Lys Gly
1               5                   10

METHOD OF INDUCING A CELL TO PROLIFERATE USING A CHIMERIC RECEPTOR COMPRISING JANUS KINASE

This application is a continuation of application Ser. No. 08/382,846, filed Feb. 2, 1995, which is pending.

INTRODUCTION

TECHNICAL FIELD

The field of this invention relates to the construction and use of novel chimeric receptor proteins for signaling cellular proliferation and optionally, for signaling cellular effector function.

BACKGROUND

The production of novel chimeric receptor proteins which initiate signaling in a cell that results in activating a second messenger pathway in response to an inducer binding to the extracellular portion of these receptors is the subject of U.S. Pat. No. 5,359,046, the entirety of which is incorporated herein by reference. These chimeric receptor molecules comprise three domains in a single protein moiety, namely, a cytoplasmic effector function signaling domain, a transmembrane domain and an extracellular inducer binding domain. The cytoplasmic domain and extracellular domain are not naturally associated together. By mixing and matching extracellular domains with a particular type of cytoplasmic domain, one may transduce a particular signal by employing different inducers that bind to different extracellular binding domain receptors. Additionally, these single molecule receptors have the desired characteristics of binding inducer and transducing a signal without requiring the major histocompatibility complex (MHC) involvement or antigen presentation. Such characteristics make these chimeric receptors ideal in the development of cellular therapies by permitting the directed activity of cells selected for a particular effector function.

To enhance the above technology, it would be desirable to insure that cells expressing these chimeric receptors with effector function are present in the body in sufficient quantity for effective cellular therapy or treatment. This requirement may be met by the proliferation of the cells expressing the chimeric effector function receptor at the site where they would be most advantageous.

The present invention provides a strategy that consists of further engineering cells, including those expressing chimeric effector function receptors such that they are capable of proliferating in the body in an inducer molecule driven fashion and, in addition, may be growth factor independent.

There is also a general need in the field for a variety of therapeutic cells to proliferate in vivo either when they have homed to or are transplanted to the proper site or in response to an administered inducer molecule. The present invention provides a method to direct cell proliferation in this manner.

SUMMARY OF THE INVENTION

Methods involving recombinant DNA technology and recombinant protein expression are provided for the production and expression of novel chimeric receptors for regulating cellular proliferation and optionally, for signaling effector function. In one general embodiment, the novel chimeric proliferation receptor proteins comprise at least an extracellular inducer-responsive clustering domain that binds to an extracellular inducer, a transmembrane domain that crosses the cell membrane, and a cytoplasmic proliferation signaling domain that signals the cell to divide upon the clustering of the extracellular domains. This novel chimeric proliferation receptor may optionally have an effector function signaling domain between the transmembrane domain and the proliferation signaling domain or it may be attached to the C-terminus of the proliferation signaling domain. In another general embodiment, the novel chimeric proliferation receptor proteins comprise at least an intracellular inducer-responsive clustering domain that binds to an intracellular inducer, and a cytoplasmic proliferation signaling domain that signals the cell to divide upon the clustering of the intracellular domains. This novel chimeric proliferation receptor may optionally have an effector function signaling domain attached via its N-terminus to the proliferation signaling domain or to the intracellular inducer-responsive clustering domain. Modifications of these receptors include amino acid substitutions or deletions of the domains, or the additions of one or more linker regions between various domains of these novel chimeric proliferation receptors.

The present invention also includes the preparation and expression of novel chimeric proliferation receptor proteins or modifications thereof by transducing into a host cell a DNA construct comprising a DNA fragment or variant thereof encoding the above novel chimeric proliferation receptor(s) functionally attached to regulatory sequences that permit the transcription and translation of the structural gene and expression in the host cell containing the DNA construct of interest.

The present invention further includes DNA fragments and variants thereof encoding the novel chimeric proliferation receptors including the expression vectors comprising the above DNA fragments or variants thereof, host cells transduced with the above expression vectors and methods of using the novel chimeric proliferation receptors to regulate cell growth or as therapeutics for treating cancer and infectious diseases.

DESCRIPTION OF THE DRAWINGS

FIGS. 2A and 2B is a listing of oligonucleotides (SEQ ID NOS:1–30) as described in the Examples, infra.

FIGS. 3 (A)–(L) are graphs of FACS analysis of CD4-Janus kinase chimeric proliferation receptor expression in 293 cells, as described in Example 10(B), infra. The dotted lines are cells stained with FITC-IgG; the solid lines are cells stained with FITC-anti-CD4.

DETAILED DESCRIPTION OF THE PREFERRED EMBODIMENTS

Figure 1:
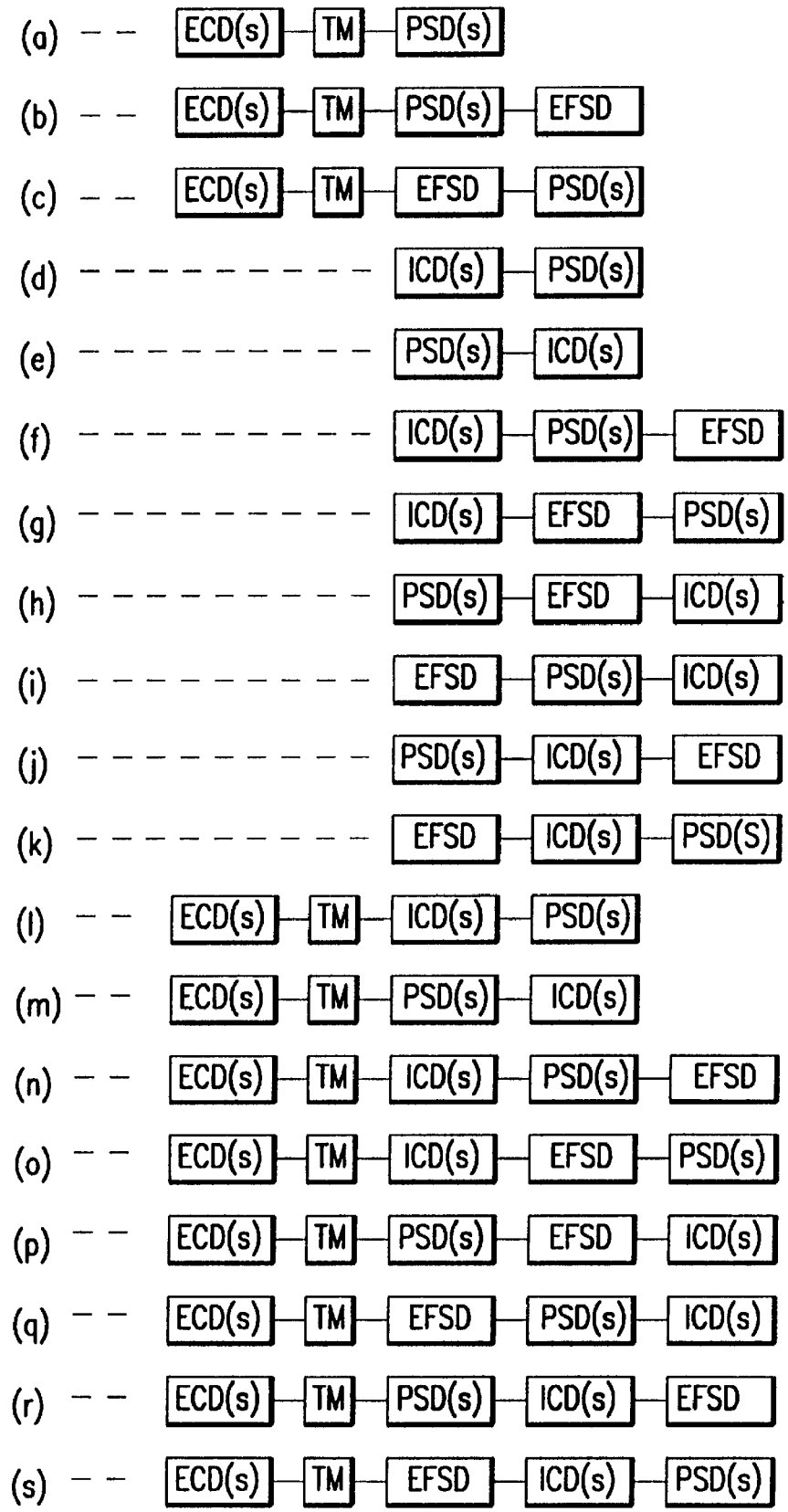
FIG. 1 illustrates the structures of the chimeric proliferation receptors discussed in the detailed description.
Figure 3A:
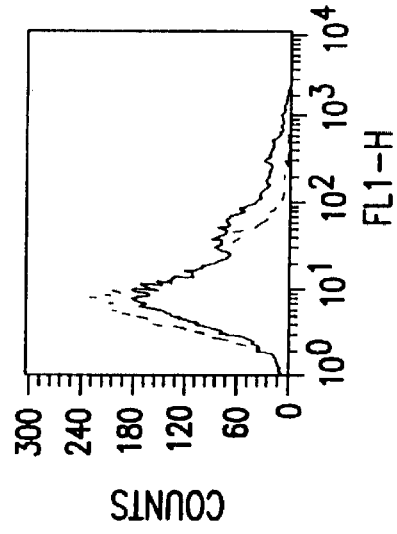
(FIG. 3(A): Mock-transfected.
Figure 3B:
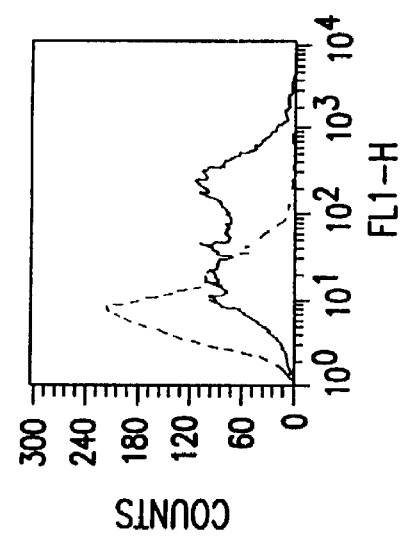
FIG. 3(B) CD4-ζ.
Figure 3C:
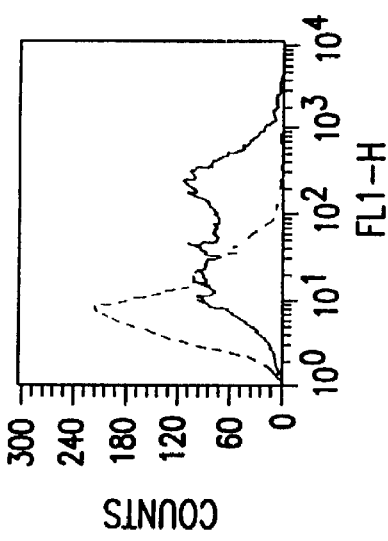
FIG. 3(C) CD4-mJAK1.
Figure 3D:
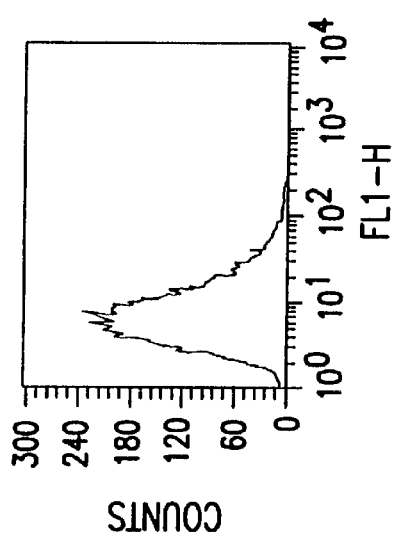
FIG. 3(D) CD4-ζ-mJAK1.
Figure 3E:
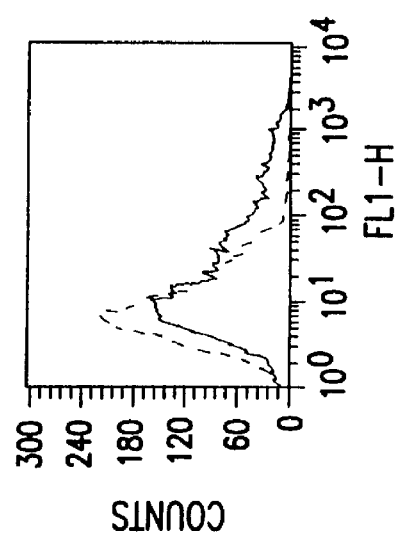
FIG. 3(E) CD4-mJAK2.
Figure 3F:
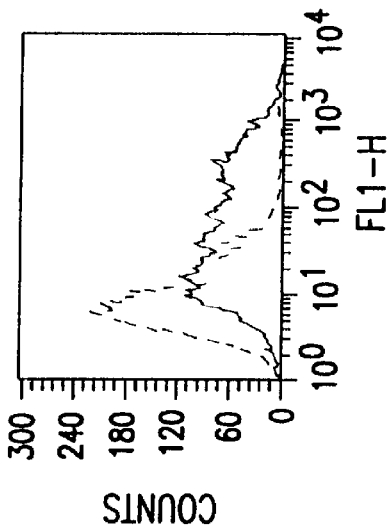
FIG. 3(F) CD4-ζ-mJAK2.
Figure 3G:
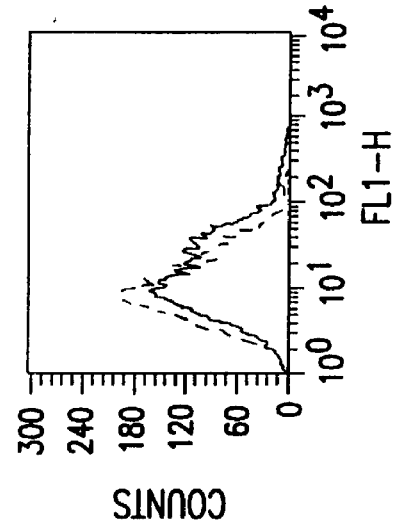
FIG. 3(G) CD4-mJAK3.
Figure 3J:
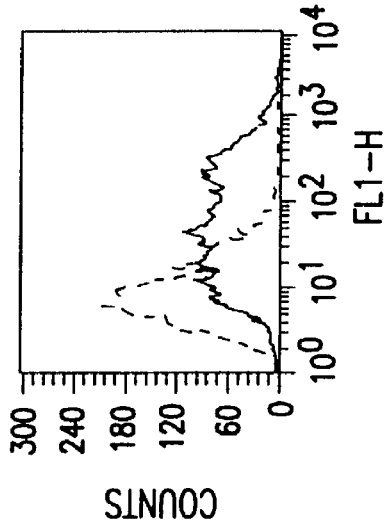
FIG. 3(J) CD4-ζ-hJAK3.
Figure 3H:
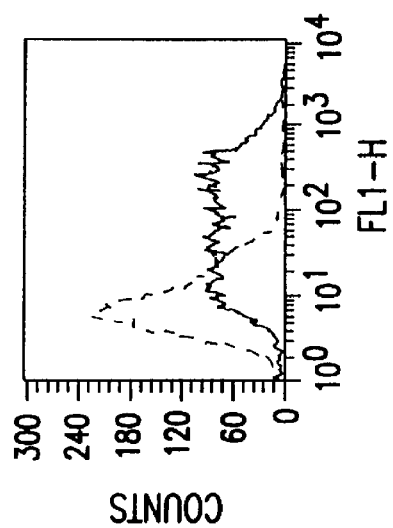
FIG. 3(H) CD4-ζ-mJAK3.
Figure 3K:
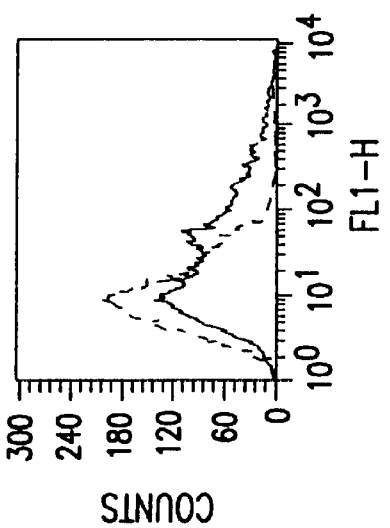
FIG. 3(K): CD4-hTyk2.
Figure 3I:
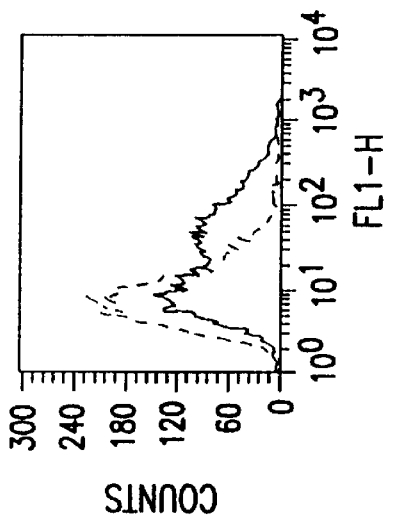
FIG. 3(I): CD4-hJAK3.
Figure 3L:
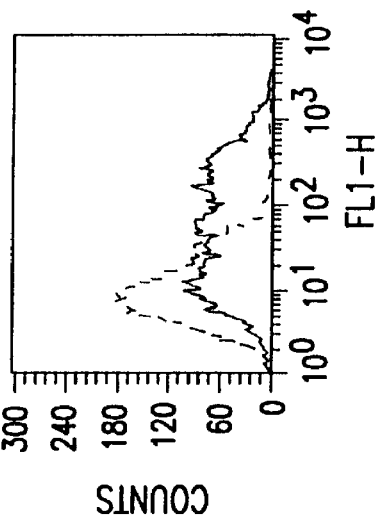
FIG. 3(L): CD4-ζ-hTyk2.)

As noted above, the present invention generally relates to novel chimeric proliferation receptor proteins and DNA sequences encoding these novel chimeric receptor proteins which may or may not additionally contain an effector function signaling domain. The novel chimeric proliferation receptors (CPRs) provided herein may be further characterized in that the inducer binding domain of the CPR is expressed extracellularly or intracellularly. CPRs may be introduced into cells already expressing a chimeric effector function receptor previously as described in U.S. Pat. No. 5,359,046 or the two receptors may be introduced together and co-expressed in the same cell. In this aspect, the CPR containing cells of the present invention have the distinct advantage of specific expansion in response to a specific inducer molecule that may simultaneously stimulate effector function in the same expanded cell population. Alternatively, CPRs of the present invention may be introduced into cells without a chimeric effector function receptor, to allow them to proliferate in vivo. Further aspects of the present invention will be discussed in detail below following a definition of terms employed herein.

Definitions:

The term "extracellular inducer-responsive clustering domain" or "ECD" refers to the portion of a protein of the present invention which is outside of the plasma membrane of a cell and binds to at least one extracellular inducer molecule as defined below. The ECD may include the entire extracytoplasmic portion of a transmembrane protein, a cell surface or membrane associated protein, a secreted protein, a cell surface targeting protein, a cell adhesion molecule, or a normally intracytoplasmic ligand-binding domain, and truncated or modified portions thereof. In addition, after binding one or more inducer molecule(s), the ECDs will become associated with each other by dimerization or oligomerization, i.e., "cluster".

The term "intracellular inducer-responsive clustering domain" or "ICD" refers to the portion of a protein which is inside of the plasma membrane of a cell, that binds to at least one intracellular inducer molecule as defined below. After binding one or more inducer molecule(s), the ICDs will become associated with each other by dimerization or oligomerization, i.e., "cluster".

The term "proliferation signaling domain" or "PSD" refers to a protein domain which signals the cell to enter mitosis and begin cell growth. Examples include the human or mouse Janus kinases, including but not limited to, JAK1, JAK2, JAK3, Tyk2, Ptk-2, homologous members of the Janus kinase family from other mammalian or eukaryotic species, the IL-2 receptor β and/or γ chains and other subunits from the cytokine receptor superfamily of proteins that may interact with the Janus kinase family of proteins to transduce a signal, or portions, modifications or combinations thereof.

The term "transmembrane domain" or "TM" refers to the domain of the protein which crosses the plasma membrane and is derived from the inducer-binding ECD domain, the effector function signaling domain, the proliferation signaling domain or a domain associated with a totally different protein. Alternatively, the transmembrane domain may be an artificial hydrophobic amino acid sequence which spans the plasma membrane.

The term "extracellular inducer molecule" refers to a ligand or antigen which binds to and induces the clustering of an ECD as described above or portions or modifications of the extracellular inducer molecule that are still capable of binding to and inducing the clustering of an ECD. To facilitate clustering, the inducer molecule may be intrinsically bivalent or multivalent; or it may be presented to the ECD in a bivalent or multivalent form, eg., on the surface of a cell or a virus.

The term "intracellular inducer molecule" refers to a natural or synthetic ligand that can be delivered to the cytoplasm of a cell, and binds to and induces the clustering of an intracellular inducer responsive domain. To facilitate clustering, the intracellular inducer molecule may be intrinsically bivalent or multivalent.

The term "chimeric extracellular inducer-responsive proliferation receptor" or "CEPR" refers to a chimeric receptor that comprises an extracellular inducer responsive clustering domain (ECD), a transmembrane domain and a proliferation signaling domain (PSD). The ECD and PSD are not naturally found together on a single receptor protein Optionally, this chimeric receptor may also contain an effector function signaling domain as defined below.

The term "chimeric intracellular inducer-responsive proliferation receptor" or "CIPR" refers to a chimeric receptor that comprises an intracellular inducer-responsive clustering domain (ICD) and a proliferation signaling domain (PSD). The ICD and PSD are not naturally found together on a single receptor protein. Optionally, this chimeric receptor may also contain an effector function signaling domain as defined below.

The term "effector function" refers to the specialized function of a differentiated cell. Effector function of a T cell, for example, may be cytolytic activity or helper activity including the secretion of cytokines.

The term "effector function signaling domain" or "EFSD" refers to the portion of a protein which transduces the effector function signal and directs the cell to perform its specialized function. While usually the entire EFSD will be employed, in many cases it will not be necessary to use the entire chain. To the extent that a truncated portion of the EFSD may find use, such truncated portion may be used in place of the intact chain as long as it still transduces the effector function signal. Examples are the ζ chain of the T cell receptor or any of its homologs (e.g., η chain, FcεR1-γ and -β chains, MB1 chain, B29 chain, etc.), CD3 polypeptides (γ, δ and ε), syk family tyrosine kinases (Syk, ZAP 70, etc.), the src family tyrosine kinases (Lck, Fyn, Lyn, etc.) and other molecules involved in T cell signal transduction.

The term "chimeric effector function receptor" refers to a chimeric receptor that comprises an extracellular domain, transmembrane domain and cytoplasmic domain as described in U.S. Pat. No. 5,359,046 or the EFSD domain as described above. The extracellular domain serves to bind to an inducer and transmit a signal to the cytoplasmic domain which transduces an effector function signal to the cell.

The term "modifications" refers to an addition of one or more amino acids to either or both of the C- and N-terminal ends of the intracellular and extracellular inducer molecules (in the case where these are proteins) or, the ECDs, ICDs, PSDs, EFSDs, or TMs, a substitution of one or more amino acids at one or more sites throughout these proteins, a deletion of one or more amino acids within or at either or both ends of these proteins, or an insertion of one or more amino acids at one or more sites in these proteins such that the inducer molecule binding to the ICD or the ECD is retained or improved as measured by binding assays known in the art, for example, Scatchard plots, or such that the PSD, EFSD or TM domain activities are retained or improved as measured by one or more of the proliferation assays described below. In addition, modifications can be made to the intracellular and extracellular inducer molecules and to the corresponding ICDs and ECDs to create an improved receptor-ligand binding pair.

The term "variant" refers to a DNA fragment encoding an intracellular or extracellular inducer molecule, or an ECD, ICD, PSD, EFSD or TM domain that may further contain an addition of one or more nucleotides internally or at the 5' or 3' end of the DNA fragment, a deletion of one or more nucleotides internally or at the 5' or 3' end of the DNA fragment or a substitution of one or more nucleotides internally or at the 5' or 3' end of the DNA fragment such that the inducer molecule binding to the ICD or the ECD is retained or improved as measured by binding assays known in the art, for example, Scatchard plots, or such that the PSD, EFSD or TM domain activities are retained or improved as measured by one or more of the proliferation assays described below. In addition, modifications can be made to the intracellular and extracellular inducer molecules and to the corresponding ICDs and ECDs to create an improved receptor-ligand binding pair.

The term "linker" or "linker region" refers to an oligo- or polypeptide region of from about 1 to 30 amino acids that links together any of the above described domains of the chimeric proliferation receptors defined above. The amino acid sequence is not derived from the ICDs, ECDs, EFSDs, PSDs, or TM domains. Examples of linker regions are linker 212 and linker 205 as referenced in Betzyk et al., *J. Biol. Chem.*, 265:18615–18620 (1990) and Gruber et al., *J. Immunol.*, 152:5368–5374 (1994) respectively.

In its general embodiments, the present invention relates to novel chimeric proliferation receptors, nucleic acid sequences encoding the receptors, the vectors containing the nucleic acid sequences encoding the receptors, the host cells expressing the receptors, and methods of using of the receptors in regulating cell growth. In one aspect of the present invention, a novel chimeric proliferation receptor (CPR) protein is provided containing an inducer-responsive binding domain and a proliferation signaling domain that do not naturally exist together as a single receptor protein. One novel CPR identified herein as "chimeric extracellular inducer responsive proliferation receptor" (abbreviated CEPR) is designed to be expressed in cells, which then proliferate in response to the binding of a specific extracellular inducer molecule. The three domains that comprise CEPR are: (1) an extracellular inducer-responsive clustering domain (ECD) which serves to bind to a ligand called an extracellular inducer molecule, (2) a transmembrane domain (TM), which crosses the plasma membrane and, (3) a proliferation signaling domain (PSD) that signals the host cell to divide. Optionally, the CEPRs described above may comprise multiple PSDs attached to each other (See FIG. 1(a)). Each inducer molecule or group of inducer molecules is presented multivalently (eg. more than one inducer molecule in close proximity to each other on a cell surface) to the CEPR. The inducer molecules will thus bind more than one ECD, causing the ECDs to dimerize or oligomerize (i.e. cluster together). This clustering transmits a signal through the transmembrane domain to the proliferation signaling domains, which become activated.

The host cells bearing the chimeric proliferation receptors of the present invention will expand in number in response to the binding of a specific extracellular inducer molecule, to the extracellular inducer-responsive clustering domain (ECD) of the CEPR. These ECDS include but are not limited to the following types of clustering domains: a cell surface or membrane associated molecule (eg, CD4, CD8, etc.), a secreted targeting molecule (eg., Interleukin-14 (IL-14), etc.), a cell surface/secreted targeting molecule (eg, antibody (Ab), single-chain antibody (SAb), antibody fragments, etc.), a cell adhesion molecule (e.g., ICAM, LFA-1, etc.), or portions or modification thereof. In each instance, the extracellular inducer molecules bind to the extracellular domains of the CEPR which results in the dimerization or oligomerization of the extracellular inducer responsive domains and hence, the dimerization or oligomerization (i.e. "clustering") of the proliferation signaling domains results in the transduction of a signal for cell growth.

If the chimeric extracellular inducer-responsive proliferation receptor (CEPR) of the present invention is expressed in host cells already expressing the chimeric effector function receptor of U.S. Pat. No. 5,359,046 described hereinabove (for example, CD4/zeta chimeric receptor), and binds to the same inducer as the CEPR, eg. CD4, then these dual chimeric receptor expressing cells will proliferate upon addition of the same inducer that drives effector function, eg. cytotoxicity. Alternatively, the inducer that binds to the extracellular binding domain of the chimeric effector function receptor may differ from the inducer molecule that binds to the ECD of the CEPR. In this case, one may separate cell growth (proliferation) from effector function in the same cell by stimulating with different inducer molecules.

In another aspect of the present invention, a novel chimeric proliferation receptor containing the proliferation signaling domain and effector function signaling domain together in the same protein receptor is provided. In this embodiment, the chimeric receptor comprises the three domains contained in the CEPR and additionally comprises an effector function signaling domain. Thus, the extracellular inducer responsive clustering domain (ECD) of the CEPR is linked via a transmembrane domain to two signal transducing domains. One signal transducing domain mediates the effector function signal while the other signal transducing domain mediates the proliferation signal, (for example, CD4-ζ-JAK1). Either the proliferation signaling domain or the effector function signaling domain may be linked to the transmembrane domain and is further linked on its 3' end to the second signaling domain either directly or through a linker region. Optionally, more than one PSD may be attached directly, or through a linker, to each other to form a CEPR with multiple PSDs (FIG. 1(b) and (c)). It is contemplated that the preparation of this novel chimeric proliferation/effector function chimeric receptor will activate proliferation and effector function simultaneously in a host cell upon the binding of extracellular inducer molecules to the ECD of the receptor.

In another embodiment, the present invention relates to a second general category of chimeric proliferation receptors called "chimeric intracellular inducer-responsive proliferation receptors" or "CIPRs". Cells constructed to express CIPRs proliferate in response to a specific ligand, called an intracellular inducer molecule. This proliferation receptor contains at least two domains: (1) an intracellular inducer-responsive clustering domain (ICD) which serves to bind to a ligand called an intracellular inducer molecule, and (2) a proliferation signaling domain (PSD) that signals the cell to divide (as an example, FKBP-JAK1). The two domains comprising a CIPR may be constructed such that either the ICD or the PSD is at the N-terminus of the CIPR. A linker region such as linker 212 (Betzyk et al., *J. Biol. Chem.* 265:18615–18620 (1990)) may also be inserted between the two domains that comprise CIPRs. Each inducer molecule binds two or more ICDs, causing them to dimerize or oligomerize (i.e. cluster together). This clustering of the ICDs causes the proliferation signaling domains to become activated. A transmembrane domain is not required but may be used in the construction of these novel intracellular proliferation receptors. Optionally, a myristylation-targeting domain may be linked to the N-terminus of the ICD or the PSD to allow for membrane association (Cross et al., *Mol.*

Cell. Biol., 4:1834–1842 (1984), Spencer et al, *Science* 262:1019–1024 (1993)). An additional option may be to construct a CIPR with more than one PSD attached directly, or through a linker, to each other (FIG. 1(*d*) and (*e*). CIPRs may be used in any host cell type for which there is a desire for regulated expansion of a therapeutic cell such as in transplantation therapy, as described infra.

The host cells bearing CIPRs of the present invention will expand in number upon binding of an intracellular inducer molecule to the intracellular inducer-responsive clustering domain (ICD) of the CIPR. These inducer molecules include but are not limited to the following ligands: natural or synthetic ligands that bind to and induce the clustering of an intracellular inducer responsive domain such as immunophilins (e.g., FKBP), cyclophilins, and steroid receptors.

The CIPRs of the present invention may also be expressed in host cells previously engineered with the chimeric effector function receptor described hereinabove. Upon addition of an extracellular inducer molecule and an intracellular inducer molecule, these cells will activate the effector function (provided by signaling through the chimeric effector function receptor) and divide (provided by signaling through the CIPR). Alternatively, the inducer that binds to the extracellular binding domain of the chimeric effector function receptor may be the same inducer as the one that binds to the ICD of the CIPR if the inducer is a intracellular inducer molecule which can be delivered to the cytoplasm of the host cell. In this situation, cell growth and effector function would be activated simultaneously in the same cell upon presentation of the intracellular inducer molecule.

In another aspect of the present invention, a novel chimeric protein receptor containing a proliferation signaling domain and effector signaling domain is provided together in the same intracellular inducer-responsive receptor (FIG. 1(*f*) through (*k*)). In this embodiment, a hybrid receptor is constructed as one protein comprising the two domains described in the CIPR of the present invention, and additionally comprising an effector function signaling domain (EFSD). Thus, the intracellular inducer responsive clustering domain (ICD) is directly connected to the proliferation signaling domain (PSD) which in turn is directly attached to an effector function signaling domain (FIG. 1(*f*)). Alternatively, the ICD may be directly connected to an effector function signaling domain which in turn is directly connected to a proliferation signaling domain (FIG. 1(*g*)). In yet another conformation of the present embodiment, either the EFSD or the PSD may be associated with the membrane via a myristylation domain or a TM domain, for example. The EFSD or the PSD is attached at its C terminus to a PSD or EFSD, respectively, which in turn is attached at its C terminus to one or more ICDs (FIG. 1(*h*) and (*i*)). In addition, CIPR proliferation/effector function receptors may be constructed by linking together the following domains (N to C terminal): a membrane-associated PSD or EFSD, followed by one or more ICDs, followed by the EFSD or PSD domain, respectively, (FIG. 1(*j*) and (*k*)). It is also possible to separate one or more domains from each other in the hybrid proliferation/effector receptors of the present embodiments with a linker region such as linker 205 (Gruber et al, *J. Tmmunol.*, 152:5368–5374 (1994)). Upon introduction of these novel hybrid chimeric proliferation/) effector function receptors into cells, one may modulate the signaling of a proliferative response and effector functional response by the addition of one or more intracellular inducer molecules.

In yet another aspect of the present invention, a novel hybrid chimeric proliferation receptor containing an extra-cellular inducer-responsive clustering domain (ECD), an intracellular inducer-responsive clustering domain (ICD), and a proliferation signaling domain (PSD) is provided together in the same receptor protein. In this embodiment, a hybrid inducer binding receptor is constructed as one protein comprising in the N-terminal to C-terminal direction an ECD, transmembrane domain, an ICD and a proliferation signaling domain (FIG. 1(*l*)). Alternatively, a hybrid inducer binding receptor is constructed as one protein comprising in the N-terminal to C-terminal direction an ECD, transmembrane domain, PSD and an ICD (FIG. 1(*m*)). In preparing the hybrid inducer binding receptors of the present embodiment, one may separate one or more domains of each receptor with a linker. Additionally, more than one ICD and PSD may be attached directly or via a linker to each other to form multiple ICDs and PSDs. Upon introduction of these novel hybrid inducer-binding chimeric proliferation receptors into a host cell, one may modulate proliferation of the cell by either an extracellular inducer, an intracellular inducer or a combination of these two different inducer molecules.

In still another embodiment, the present invention provides a chimeric proliferation receptor described above containing an ECD, TM, ICD and PSD (N- to C-terminal) that additionally contains an effector function signaling domain (EFSD) attached at the N-terminal (FIG. 1(*o*)) or C-terminal (FIG. 1(*n*)) end of the PSD. Multiple ECDs, ICDs and/or PSDs may be used in the construction of the above receptors. Additional embodiments of hybrid CPRs containing one or more ICD(s) and ECD(s) and one or more PSD(s) and one EFSD are contemplated that comprise the following four conformations (N- to C-terminus): ECD(s), TM, PSD(s), EFSD and ICD(s) (FIG. 1(*p*)); ECD, TM, EFSD, PSD and ICD (FIG. 1(*q*)); ECD(s), TM, PSD(s), ICD(s) and EFSD (FIG. 1(*r*)); and ECD(s), TM, EFSD, ICD(s) and PSD(s) (FIG. 1(*s*)). Upon expression of these novel proliferation/effector receptors in a host cell, one may modulate proliferation and effector signaling by adding either an extracellular inducer, an intracellular inducer or a combination of these two different inducer molecules.

The proliferation signaling domains (PSDs) that comprise the chimeric proliferation receptors (CPRs) of the present invention (both CIPRs and CEPRs) may be obtained from the cytoplasmic signal-transducing domains of the cytokine/hematopoietin receptor superfamily. The members of this mammalian receptor superfamily can transduce proliferative signals in a wide variety of cell types. These receptors are structurally related to each other. The cytoplasmic domains of the signal-transducing subunits may contain conserved motifs that are critical for transduction of proliferative signals (Bazan, *Current Biology*, 3:603–606 (1993); Boulay and Paul, *Current Biology*, 3:573–581 (1993); Wells, *Current Opinion in Cell Biology*, 6:163–173 (1994); Sato and Miyajima, *Current Opinion in Cell Biology*, 6:174–179 (1994); Stahl and Yancopoulos, *Cell*, 74:587–590 (1993); Minami et al., *Ann. Rev. Immunol.*, 11:245–267 (1993); Kishimoto et al., *Cell*, 76:253–262 (1994)). In contrast to the growth factor receptors previously described in chimeric receptors (Schlessinger and Ullrich , *Cell*, 61:203–212 (1990), Ullrich and Schlessinger, *Neuron*, 9:383–391 (1992) ), the cytoplasmic portions of the cytokine receptor superfamily proteins that comprise the PSDs employed in the present invention do not contain any kinase domains or other sequences with recognizable catalytic function. Further, although the growth factor receptors described by Ullrich and the cytokine receptors employed in the present invention both dimerize upon binding of inducer, the dimerized growth factor receptors activate their intrinsic receptor kinase activity, while the dimerized cytokine receptors employed in the present invention stimulate the activity of associated tyrosine kinases (Kishimoto et al., *Cell*, 76:253–262 (1994)). The signal-transducing components of the cytokine receptors to be used in the PSDs of the present invention include, but are not limited to, Interleukin-2 receptor β (IL-2Rβ), IL-2Rγ, IL-3Rβ, IL-4R, IL-5Rα, IL-5Rβ, IL-6R, IL-6R gp130, IL-7R, IL-9R, IL-12R, IL-13R, IL-15R, EPO-R (erythropoietin receptor), G-CSFR (granulocyte colony stimulating factor receptor), GM-CSFRα (granulocyte macrophage colony stimulating factor receptor α), GM-CSFRβ, LIFRα (leukemia inhibitory factor receptor α), GHR (growth hormone receptor), PRLR (prolactin receptor), CNTFR (ciliary neurotrophic factor receptor), OSMR (oncostatin M receptor) IFNRα/β (interferon α/β receptor), IFNRγ, TFR (tissue factor receptor),and TPOR (thrombopoietin or mpl-ligand receptor)(Minami et al., *J. Immunol.*, 152:5680–5690 (1994); Boulay and Paul, *Current Biology*, 3:573–581 (1993); Wells, *Current Opinion in Cell Biology*, 6:163–173 (1994)).

The IL-2, IL-3 and IL-6 subfamilies of the above cytokine receptor superfamily, which are active in many different cell types, may supply the PSDs of the CPRs of the present invention. The IL-2 receptor subfamily includes, but is not to be limited to, the receptors for IL-2, IL-4, IL-7, IL-9, IL-13 and IL-15. IL-2R, IL-4R, IL-7R, IL-9R, IL-13R and IL-15R share IL-2Rγ, one of the signal transducing components of the IL-2R (Noguchi et al., *Science*, 262:1877–1880 (1993); Russel et al., *Science*, 262:1880–1884 (1993); Minami et al., *J. Immunol.*, 152:5680–5690 (1994)). IL-2R and IL-15R share a second transducing component, IL-2Rβ (Giri et al., *EMBO J.*, 13:2822–2830 (1994)). These cytokines act on a wide variety of cell types, for example, B cells, T cells including LAK cells and thymocytes, NK cells, and oligodendroglial cells (Kishimoto et al., *Cell*, 76:253–262 (1994)). In addition, high affinity receptors to IL-15 are found on myeloid cells, vascular endothelial cells, and on stromal cells types from bone marrow, fetal liver and thymic epithelium (Giri et al., *EMBO J.*, 13:2822–2830 (1994)). The IL-3 receptor subfamily includes, but is not limited to, the receptors for IL-3, IL-5 and GM-CSF (Sato and Miyajima, *Current Opinion in Cell Bioloay*, 6:174–179 (1994)). These cytokine receptors contain a common signal-transducing, or β chain which has a large cytoplasmic domain whose membrane proximal region is critical for c-myc induction and proliferative signaling activity (Quelle et al.,*Mol. Cell. Biol.*, 14:4335–4341 (1994)). This family of cytokines act on overlapping cell types during hematopoiesis including blast cells, granulocytes, macrophages, monocytes and eosinophils (Kishimoto et al., *Cell*, 76:253–262 (1994)). The IL-6 receptor subfamily includes, but is not limited to, the receptors for IL-6, CNTF, LIF, OSM, IL-11, G-CSFR and IL-12. IL-6R, CNTFR, LIFR and OSMR have a common signal-transducing chain (gp130) with a cytoplasmic domain whose membrane proximal region is critical for signaling activity (Sato and Miyajima, *Current Opinion in Cell Biology*, 6:174–179 (1994), Narazaki et al., *Proc. Natl. Acad. Sci.*, 91:2285–2289 (1994)). These cytokines act on a wide variety of cell types, including ciliary, sympathetic, sensory and motor neurons, embryonic stem cells, control of the differentiation of B cells, plasmacytomas, megakaryocytes, myeloid cells, osteoclasts, and hepatocytes (Kishimoto et al., *Cell*, 76:253–262 (1994)). Other members of the cytokine receptor superfamily which may be a part of the above subfamilies, or may be members of novel subfamilies include the receptors for EPO, TPO, GH and PRL, which are also found on many cell types (Wells, *Current Opinion in Cell Biology*, 6:163–173 (1994), Stahl and Yancopoulos, *Cell*, 74:587–590 (1993)). The more distantly related IFNα/β and IFNγ receptors, found in most cell types also contain cytoplasmic domains of related structure (Farrar and Schreiber, *Annu. Rev. Immunol.*, 11:571–611 (1993), Taga and Kishimoto, *FASEB J.*, 6:3387–3396 (1992)).

The proliferation signaling domains employed in constructing the CPRs of the present invention may also be obtained from any member of the Janus or JAK eukaryotic family of tyrosine kinases, including Tyk2, JAK1, JAK2, JAK3 and Ptk-2. Members of the Janus kinase family are found in all cell types. They associate with various signal transducing components of the cytokine receptor superfamily discussed above and respond to the binding of extracellular inducer by the phosphorylation of tyrosines on cytoplasmic substrates (Stahl and Yancopoulos, *Cell*, 74:587–590 (1993)). They are thus an integral part of the control of cell proliferation in many different kinds of cells. The members of this family are marked by similar multi-domain structures and a high degree of sequence conservation. Unique among tyrosine kinases, the Janus kinase family may have two non-identical tandem kinase-like domains, only one of which may have catalytic activity (Firmbach-Kraft et al., *Oncopene*, 5:1329–1336 (1990); Wilks et al., *Mol. Cell. Biol.*, 11:2057–2065 (1991); Harpur et al., *Oncogene*, 7:1347–1353 (1992)). The Janus kinases used in the present invention, unlike the src kinases, do not have src homology sequences (SH2, SH3) or a consensus sequence for myristylation. Unlike the receptor tyrosine kinases (RTK), the Janus kinases are not membrane proteins and do not contain transmembrane spanning domains (Ullrich and Schlessinger, *Neuron*, 9:383–391 (1992)). The kinase activity of the Janus kinases is usually activated after the binding of inducers to their associated cytokine family receptors and the oligomerization of the receptors (Stahl and Yancopoulos, *Cell*, 74:587–590 (1993)). This activation, in turn, triggers the initiation of intracellular signaling cascades.

JAK3 can be employed as a PSD in any of the CPRs of the present invention. Its activation by IL-2 parallels c-myc induction and the onset of DNA synthesis. JAK3 is involved with IL-2, IL-4 and IL-7 induced stimulation of T, NK and myeloid cells (Witthuhn et al., *Nature*, 370:153–157 (1994); Russell et al., *Science*, 366:1042–1044 (1994); Kawamura et al., *Proc. Natl. Acad. Sci.*, 91:6374–6378 (1994); Miyazaki et al., *Science*, 266:1045–1047 (1994); Johnston et al., *Nature*, 370:151–153 (1994); Asao et al., *FEBS Letters*, 351:201–206 (1994), Zeng et al., *FEBS Letters*, 353:289–293 (1994)). JAK2, a component of growth factor signaling in a wider variety of cells, can also be used in the CPRs of the present invention. It is activated by EPO, GH, prolactin, IL-3, GM-CSF, G-CSF, IFNγ, LIF, OSM, IL-12 and IL-6 (Watling et al., *Nature*, 366:166–170 (1993); Witthuhn et al., *Cell*, 74:227–236 (1993); Argetsinger et al., *Cell*, 74:237–244 (1993); Stahl et al., *Science*, 263:92–95 (1994); Narazaki et al., *Proc. Natl. Acad. Sci.*, 91:2285–2289(1994); Quelle et al., *Mol. Cell. Biol.*, 14:4335–4341 (1994); Silvennoinen et al., *Nature*, 366:583–585 (1993); Darnell et al., *Science*, 264:1415–1421 (1994)Campbell et al, *Proc. Natl. Acad. Sci.*, 91:5232–5236 (1994), Bacon et al., *J. Exp. Med.*, 181:399–404 (1995); (Harpur *Oncogene* 7: 1347–1353, 1992)). The present invention also contemplates the use of JAK1 as a PSD in the present invention. Its activity is also promiscuous, being an integral part of IFNR-α, IFNR-γ, IL-2Rβ, IL-6R and CNTFR signaling (Muller et al., *Nature*, 366:129–135 (1993); Silvennoinen et al., *Nature*, 366:583–585 (1993); Stahl et al., *Science*, 263:92–95 (1994), Tanaka et al., *Proc. Natl. Acad. Sci.*, 91:7271–7275 (1994)). Tyk2, which may also be employed as a PSD, is involved with IFN-α, IL-6, IL-12, and CNTF induced signaling (Velazquez et al., *Cell*, 70:313–322 (1992); Silvennoinen et al., *Nature*, 366:583–585 (1993); Stahl et al., *Science*, 263:92–95 (1994); Colamonici et al., *J. Biol. Chem.*, 269:3518–3522 (1994); Darnell et al., *Science*, 264:1415–1421 (1994), Bacon et al., *J. Exp. Med.*, 181:399–404 (1995)) and is found in both hematopoietic and non-hematopoietic tissues (Firmbach-Kraft et al., *Oncogene* 5: 1329–1336, 1990). In addition to the Janus kinases described above, a new JAK kinase Ptk-2 has recently been described in embryonic hippocampal neurons (Sanchez et al. *Proc. Natl. Acad. Sci.*, 91:1819–1823 (1994), and can be used to form the proliferation signaling domain of any of the chimeric proliferation receptor proteins of the present invention.

One may introduce the CPR into cells where the PSD being used is not naturally found in those cells or is part of a pathway which is ordinarily not active in those cells. This unnatural expression of a particular Janus kinase or cytokine receptor subunit may have added utility. For example, if the PSDs are more active in this unnatural location, they may be more efficient stimulators of proliferation. Alternatively, if the PSDs are less active in the unnatural location they may be less likely to be constitutively active and thus more responsive to an inducer.

The transmembrane domain may be contributed by the protein contributing the proliferation signaling portion, the protein contributing the extracellular inducer clustering domain, or by a totally different protein. For the most part it will be convenient to have the transmembrane domain naturally associated with one or the other of the other domains. In some cases it will be desirable to employ the transmembrane domain of the ζ, η or FcεR1γ chains or related proteins which contain a cysteine residue capable of disulfide bonding, so that the resulting chimeric protein will be able to form disulfide linked dimers with itself, or with unmodified versions of the ζ, η or FcεR1γ chains or related proteins. In some instances, the transmembrane domain will be selected or modified by amino acid substitution to avoid binding of such domains to the transmembrane domains of the same or different surface membrane proteins to minimize interactions with other members of the receptor complex. In other cases it will be desirable to employ the transmembrane domain of ζ, η, FcεR1-γ and -β, MB1 (Ig α), B29 (Igβ), Bovine Leukemia Virus gp30 (BLV gp30), or CD3-γ, δ, or ε, in order to retain physical association with other members of the receptor complex.

The CPRs of the present invention may be designed so as to avoid interaction with other surface membrane proteins native to the target host. In order to achieve this, one may select for a transmembrane domain which is known not to bind to other transmembrane domains, or one may modify specific amino acids, e.g. substitute for a cysteine, or the like.

The extracellular inducer-responsive clustering domain (ECD) may be obtained from any of the wide variety of extracellular domains of eukaryotic transmembrane proteins, secreted proteins or other proteins associated with ligand binding and/or signal transduction. The ECD may be part of a protein which is monomeric, homodimeric, heterodimeric, or associated with a larger number of proteins in a non-covalent or disulfide-bonded complex.

In particular, the ECDs may consist of monomeric or dimeric immunoglobulin molecules, or portions or modifications thereof, which are prepared in the following manner.

The full-length IgG heavy chain comprising the VH, CH1, hinge, and the CH2 and CH3 (Fc) Ig domains is fused to the proliferation signaling domain (PSD) via the appropriate transmembrane domain. If the VH domain alone is sufficient to confer antigen-specificity (so-called "single-domain antibodies"), homodimer formation of the Ig-PSD chimera is expected to be functionally bivalent with regard to antigen binding sites. If both the VH domain and the VL domain are necessary to generate a fully active antigen-binding site, both the IgH-PSD molecule and the full-length IgL chain are introduced into cells to generate an active antigen-binding site. Dimer formation resulting from the intermolecular Fc/hinge disulfide bonds results in the assembly of Ig-PSD receptors with extracellular domains resembling those of IgG antibodies. Derivatives of this Ig-PSD chimeric receptor include those in which only portions of the heavy chain are employed in the fusion. For example, the VH domain (and the CH1 domain) of the heavy chain can be retained in the extracellular domain of the Ig-PSD chimera (VH-PSD), but VH-PSD dimers are not formed. As above, the full-length IgL chain can be introduced into cells to generate an active antigen-binding site.

As indicated, the ECD may consist of an Ig heavy chain which may in turn be covalently associated with Ig light chain by virtue of the presence of the CH1 region, or may become covalently associated with other Ig heavy/light chain complexes by virtue of the presence of hinge, CH2 and CH3 domains. The two heavy/light chain complexes may have different specificities, thus creating a CPR which binds two distinct antigens. Depending on the function of the antibody, the desired structure and the signal transduction, the entire chain may be used or a truncated chain may be used, where all or a part of the CH1, CH2, or CH3 domains may be removed or all or part of the hinge region may be removed.

Because association of both the heavy and light V domains are required to generate a functional antigen binding site of high affinity, in order to generate a Ig chimeric receptor with the potential to bind antigen, a total of two molecules will typically need to be introduced into the host cell. Therefore, an alternative and preferred strategy is to introduce a single molecule bearing a functional antigen binding site. This avoids the technical difficulties that may attend the introduction and coordinated expression of more than one gene construct into host cells. This "single-chain antibody" (SAb) is created by fusing together the variable domains of the heavy and light chains using an oligo- or polypeptide linker, thereby reconstituting an antigen binding site on a single molecule.

Single-chain antibody variable fragments (SAbFv) in which the C-terminus of one variable domain (VH or VL) is tethered to the N-terminus of the other (VL or VH, respectively), via a oligo- or polypeptide linker, have been developed without significantly disrupting antigen binding or specificity of the binding (Bedzyk et al. (1990) *J. Biol. Chem.*, 265:18615; Chaudhary et al. (1990) *Proc. Natl. Acad. Sci.*, 87:9491). The SAbFvs used in the present invention may be of two types depending on the relative order of the VH and VL domains: VH-l-VL or VL-l-VH (where "l" represents the linker). These SAbFvs lack the constant regions (Fc) present in the heavy and light chains of the native antibody. In another aspect of the present invention, the SAbFv fragment may be fused to all or a portion of the constant domains of the heavy chain, and the resulting ECD is joined to the PSD via an appropriate transmembrane domain that will permit expression in the host cell. The resulting CPRs differ from the SAbFvs, described above, in that upon binding of antigen they initiate signal transduction via their cytoplasmic domain.

To aid in the proper folding and efficient expression of the CPRs, the antibody-derived ECDs may be connected at their C-terminal end to one of a number of membrane hinge regions which are a normal part of membrane-bound immunoglobulin molecules. For example, the eighteen amino acids of the IGHG3 M1 exon may be used (Bensmana and Lefranc, *Immunogenet.*, 32:321–330 (1990)). The TM domain is attached to the C-terminal end of the membrane hinge. It is also contemplated that membrane hinge sequences may be used to connect non-antibody derived ECDs to the transmembrane domains to increase CPR expression.

Diabodies may also be used as ECDs in the present invention. Diabodies contain two chimeric immunoglobulin chains, one of which comprises a VH domain connected to a VL domain on the same polypeptide chain (VH-VL). A linker that is too short to allow pairing of the VH and VL domains on this chain with each other is used so that the domains will pair with the complementary VH and VL domains on the other chimeric immunoglobulin chain to create two antigen-binding sites (Holliger et al., *Proc. Natl. Acad. Sci.* 90:6444–6448 (1993)). As described above, one of these chains is linked to the membrane hinge and/or the TM domain, which in turn is linked to the PSD and/or ESD. The other chain (not connected to a PSD) will be co-expressed in the same cell to create a CPR with a diabody ECD which will respond to two different extracellular inducer molecules.

Various naturally occurring receptors may also be employed as ECDs, where the receptors are surface membrane proteins, including cell differentiation antigens such as CD4 and CD8, cytokine or hormone receptors or cell adhesion molecules. The receptor may be responsive to a natural ligand, an antibody or fragment thereof, a synthetic molecule, e.g., drug, or any other agent which is capable of inducing a signal. In addition, either member of a inducer/receptor pair, where one is expressed on a target cell such as a cancer cell, a virally infected cell or an autoimmune disease causing cell, may also be used as an ECD in the present invention. In addition, the receptor-binding domains of soluble protein ligands or portions thereof could be employed as ECDs in the CPRs of the present invention. In addition, for example, binding portions of antibodies, cytokines, hormones, or serum proteins can be used. In addition, the soluble components of the cytokine receptors such as IL-6R, IL-4R, and IL-7R can be used (Boulay and Paul *Current Biology* 3: 573–581, (1993)).

"Hybrid" ECDs can also be used in the present invention. For example, two or more antigen-binding domains from antibodies of different specificities, two or more different ligand-binding domains, or a combination of these domains can be connected to each other by oligo- or polypeptide linkers to create multispecific extracellular binding domains. These ECDs can be used to create CPRs of the present invention which will respond to two or more different extracellular inducer molecules. (See FIG. 1(*a*)–(*c*) and (1)–(*s*) that illustrate the above embodiment).

Where a receptor is a molecular complex of proteins, where only one chain has the major role of binding to the ligand, it will usually be desirable to use solely the extracellular portion of the ligand binding protein. Where the extracellular portion may complex with other extracellular portions of other proteins or form covalent bonding through disulfide linkages, one may also provide for the formation of such dimeric or multimeric extracellular regions. Also, where the entire extracellular region is not required, truncated portions thereof may be employed, where such truncated portion is functional. In particular, when the extracellular region of CD4 is employed, one may use only those sequences required for binding of gp120, the HIV envelope glycoprotein. In the case in which Ig is used as the extracellular region, one may simply use the antigen binding regions of the antibody molecule and dispense with the constant regions of the molecule (for example, the Fc region consisting of the CH2 and CH3 domains).

In some instances, a few amino acids at the joining region of the natural protein domain may be deleted, usually not more than 30, more usually not more than 20. Also, one may wish to introduce a small number of amino acids at the borders, usually not more than 30, more usually not more than 20. The deletion or insertion of amino acids will usually be as a result of the needs of the construction, providing for convenient restriction sites, ease of manipulation, improvement in levels of expression, proper folding of the molecule or the like. In addition, one may wish to substitute one or more amino acids with a different amino acid for similar reasons, usually not substituting more than about five amino acids in any one domain. The PSD, ECD, EFSD and ICD will generally be from about 50 to 1500 amino acids, depending upon the particular domain employed, while the transmembrane domain will generally have from about 20 to 35 amino acids.

Normally, the signal sequence at the 5' terminus of the open reading frame (ORF) which directs the chimeric protein to the surface membrane will be the signal sequence of the ECD. However, in some instances, one may wish to exchange this sequence for a different signal sequence. However, since the signal sequence will be removed from the protein during processing, the particular signal sequence will normally not be critical to the subject invention.

Extracellular inducers of the present invention can be antigens which bind the ECDs, described above. These may include viral proteins, (e.g. gp120 and gp41 envelope proteins of HIV, envelope proteins from the Hepatitis B and C viruses, the gB and other envelope glycoproteins of human cytomegalovirus, the envelope proteins from the Kaposi's sarcoma-associated herpesvirus), and surface proteins found on cancer cells in a specific or amplified fashion, (eg the IL-14 receptor, CD19 and CD20 for B cell lymphoma, the Lewis Y and CEA antigens for a variety of carcinomas, the Tag72 antigen for breast and colorectal cancer, EGF-R for lung cancer, and the HER-2 protein which is often amplified in human breast and ovarian carcinomas). For other receptors, the receptors and ligands of particular interest are CD4, where the ligand is the HIV gp120 envelope glycoprotein, and other viral receptors, for example ICAM, which is the receptor for the human rhinovirus, and the related receptor molecule for poliovirus.

The intracellular clustering domain (ICD) can be obtained from the inducer binding domains of a variety of intracellular proteins. For example, eukaryotic steroid receptor molecules can be used as ICDs (e.g. the receptors for estrogen, progesterone, androgens, glucocorticoids, thyroid hormone, vitamin D, retinoic acid, 9-cis retinoic acid and ecdysone). In addition, variants of steroid and other receptors which fail to bind their native inducer, but still bind to an antagonist, can be prepared by one skilled in the art and used to make the CPRs of this invention. For example, a C-terminal deletion mutant of the human progesterone receptor, which fails to bind progesterone, can be clustered by the addition of progesterone antagonists, including RU 486 (Wang et al., *Proc Natl Acad Sci* 91: 8180–8184, 1994).

Binding domains from the eukaryotic immunophilin family of molecules may also be used as ICDs. Examples include but are not limited to members of the cyclophilin family: mammalian cyclophilin A, B and C, yeast cyclophilins 1 and 2, Drosophila cyclophilin analogs such as ninaA; and members of the FKPB family: the various mammalian isoforms of FKBP and the FKBP analog from Neurospora (Schreiber, *Science*, 251:283–287 (1991), McKeon, *Cell*, 66:823–826, (1991), Friedman and Weissman, *Cell*, 66:799–806, (1991), Liu et al., *Cell*, 66:807–815 (1991)). For example, the inducer binding portion of the immunophilin, FKBP12, which can be clustered in the cytoplasm by the addition of FK1012, a synthetic dimeric form of the immunosuppressant FK506 (Spencer et al., *Science* 262: 1019–1024 (1993) can be used as an ICD.

The intracellular inducers of the present invention must be molecules which can be delivered to the cytoplasm. For example, the inducer may be lipophilic, or be transported into the cell by active transport or pinocytosis, by fusion with a liposome carrying the inducer, or by semi-permeabilization of the cell membrane. The intracellular inducers cluster the ICDs which make up the CIPRs of the present invention. Examples of inducers include, but are not limited to synthetic dimeric molecules such as FK1012 (Spencer et al., *Science*, 262:1019–1024 (1993)) or dimeric derivatives of the binding domains of other immunophilin binding molecules such as cyclosporin, rapamycin and 506BD (Schreiber, *Science*, 251:283–287 (1991), McKeon, *Cell*, 66:823–826, (1991)). Steroids, such as estrogen, progesterone, the androgens, glucocorticoids, thyroid hormone, vitamin D, retinoic acid, 9-cis retinoic acid or ecdysone, or antagonists or derivatives of these molecules may also be used as intracellular inducer molecules. In particular the steroid antagonist RU 486 may be used (Wang et al., *Proc. Natl. Acad. Sci.*, 91:8180–8184 (1994)).

The effector function signaling domains (EFSDs) employed in the present invention may be derived from a protein which is known to activate various second messenger pathways. One pathway of interest is that involving phosphatidylinositol-specific phospholipase hydrolysis of phosphatidylinositol-4,5-biphosphate, and production of inositol-1,4,5-trisphosphate and diacylglycerol. The calcium mediated pathway, the tyrosine and serine/threonine kinase and phosphatase pathway, the adenylate cyclase, and the guanylate cyclase pathways may also be second messenger pathways. EFSDs of interest include proteins with ARAM motifs (Reth, *Nature*, 338:383–384 (1989), Weiss, *Cell*, 73:209–212, (1993)), for example, the ζ chain of the T-cell receptor, the η chain, which differs from the ζ chain only in its most C-terminal exon as a result of alternative splicing of the ζ mRNA, the γ and β subunits of the FcεR1 receptor, the MB1 (Igα) and B29 (Igβ) chains of the B cell receptor, the BLV gp30 protein and the δ, γ, and ε chains of the T-cell receptor (CD3 chains), other protein homologous to the above protein subunits including synthetic polypeptides with ARAM motifs, and such other cytoplasmic regions which are capable of transmitting a signal as a result of interacting with other proteins capable of binding to a inducer (Romeo et al., *Cell*, 68:889–897 (1992); Weiss, *Cell*, 73:209–212 (1993)). The syk family of tyrosine kinases may also be used as effector function signaling domains. The clustering of these domains from Syk and ZAP-70 leads to the activation of T cell cytolytic activity (Kolanus et al., *Cell*, 74:171–183 (1993)). In addition, the src family of tyrosine kinases (Lck, Fyn, Lyn, etc.(Rudd et al., *Immunology Today*, 15:225–234 (1994)) and molecules involved in T cell transduction may be used as EFSDs in the present invention. A number of EFSDs or functional fragments or mutants thereof may be employed, generally ranging from about 50 to 1500 amino acids each, where the entire naturally occurring cytoplasmic region may be employed or only an active portion thereof.

The CPRs of the present invention are employed in a wide variety of target host cells, normally cells from vertebrates, more particularly, mammals, desirably domestic animals or primates, particularly humans. In particular, the subject invention may also find application in the expansion of lymphoid cells, e.g., T lymphocytes, B lymphocytes, cytotoxic lymphocytes (CTL), natural killer cells (NK), tumor-infiltrating-lymphocytes (TIL) or other cells which are capable of killing target cells when activated. In addition, suitable host cells to introduce CPRs of the present invention include hematopoietic stem cells, which develop into cytotoxic effector cells with both myeloid and lymphoid phenotype including granulocytes, mast cells, basophils, macrophages, natural killer (NK) cells and T and B lymphocytes. In particular, diseased cells, such as cells infected with HIV, HTLV-I or II, cytomegalovirus, hepatitis B or C virus, *Mycobacterium avium*, etc., neoplastic cells, or autoimmune disease-causing cells where the diseased cells have a surface marker associated with the diseased state may be made specific targets of the cells expressing the CPRs of the present invention. In the present invention, a cell may express dual CEFR and CPR receptors, which contain the same extracellular binding domain (eg. CD4), or a cell may express a hybrid chimeric receptor combining both signaling domains (EFSD and PSD). In each case, the binding of one inducer to the extracellular binding domain will stimulate cells to act as therapeutic agents at the same time they are expanding in response to binding to inducer, e.g., gp120 for HIV or cancer-specific antigens.

In a preferred embodiment, the present invention relates to the design of chimeric proliferation receptor (CPR) molecules which can endow T cells with the ability to proliferate in an antigen-specific and IL-2 independent manner. A T cell ordinarily requires as many as three distinct stimuli to become fully activated and begin to proliferate. It must receive two signals from the antigen presenting cell (APC). The first of these signals occurs upon engagement of the T cell antigen receptor with the peptide antigen-MHC complex. The second costimulatory signal is provided through the interaction of the CD28 or CTLA4 proteins on the T cell surface with either the B7-2 or B7 proteins, their counter-receptors on the APC (Clark and Ledbetter, *Nature*, 367:425–428 (1994); Croft, *Current Opinion in Immunology*, 6:431–437 (1994)). In addition to these two signals provided during cell to cell contact between the T cell and APC, it is apparent that certain cytokines, for example IL-2, play an important role in initiating and sustaining ongoing proliferation of activated T cells (Taniguchi and Minami, *Cell*, 73:5–8 (1993)). The antigen receptor-mediated signal (e.g., anti-CD3 MAb) and the costimulatory signal (e.g., APC) play an important role in initiating and sustaining T cell proliferation, for example, by inducing IL-2 receptors which will in turn make the T cell responsive to autocrine or exogenous IL-2 stimulation. Chimeric proliferation receptors for T cells can route an antigen signal directly through the IL-2 signaling apparatus, and bypass the need to engage the T cell receptor and costimulatory receptor to elicit T cell proliferation, while still maintaining antigen specificity. This chimeric receptor will link an ECD which is an antigen binding moiety such as an antibody or a viral receptor (e.g., CD4, the receptor for HIV) to a proliferation signaling domain which is a component of the IL-2R. One embodiment of the CPR invention would be to use one of the subunits of the IL-2 receptor (IL-2R) as a proliferation signaling domain. Specifically, the β and γ chains of the IL-2R may be utilized as PSDs in the present invention. Alternatively, the CPRs may incorporate both of all or part of the transducing domains of the IL-2Rβ and γ, which are connected through the use of an appropriate polypeptide linker sequence, in a single chimeric receptor. In a further embodiment, the CPR containing the IL-2Rβ PSD or the IL-2Rγ PSD alone is complemented with the native form of IL-2R γ or IL-2Rβ subunit respectively, which is provided by transduction. It is further contemplated that the signal transducing domains of the cytokine receptor superfamily described above may function as the PSDs in the CPRs in T cells of the present invention. In a further embodiment, chimeric proliferation receptors may incorporate more than one signaling domain chosen from the cytokine receptor family, which may be connected through an appropriate oligo- or polypeptide linker sequence in a single chimeric receptor.

In another preferred embodiment, the present invention relates to the use of chimeric proliferation receptors to induce the proliferation of T cells, where the proliferation signaling domains are comprised of one or more of the family of Janus kinases, i.e., JAK1, JAK2, JAK3, Tyk2 and Ptk-2. In the most preferred embodiment, either JAK1 or JAK3 alone or together may be employed as the PSD(s) since they play a critical role in IL-2 induced proliferation of T cells: The kinase activity of both JAK1 and JAK3 becomes stimulated after IL-2 binding to the IL2R. JAK1 and JAK3 are associated with the membrane proximal regions of the IL-2Rβ and γ chains, respectively, which are integral to the transmission of proliferative stimuli (Asao et al., *FEBS Letters*, 351:201–206 (1994); Johnston et al., *Nature*, 370:151–153 (1994); Miyazaki et al., *Science*, 266:1045–1047 (1994); Russell et al., *Science*, 366:1042–1044 (1994); Witthuhn et al., *Nature*, 370:153–157 (1994)). However, as discussed above, a Janus kinase or cytokine receptor family subunit which is not naturally found or used in a given cell may be of particular utility as a PSD, in that such a molecule may either have greater kinase activity and thus be more efficient at promoting cell growth, or it may have less constitutive activity and thus be more readily modulated by clustering.

In yet another preferred embodiment, the present invention relates to T cells containing single chimeric polypeptide receptors that drive both proliferation and effector function through the same inducer molecule. Thus, the extracellular inducer-responsive clustering domain is linked via a transmembrane domain to two signal transducing domains in tandem. One signal transducing domain contains the proliferation signal (as described above) while the other signal transducing domain contains an effector function signal. In a particularly preferred embodiment, the effector signaling domain from a member of the Syk tyrosine kinase family which activates cytolysis, Syk or ZAP-70, is in a chimeric receptor with a proliferation signaling domain from a Janus kinase, JAK1, JAK2, JAK3, Tyk2 or Ptk-2.

In another particularly preferred embodiment, the effector function signaling domain from ζ, η, the FcεR1-β and -γ chains, MB1 (Igα) and B29 (Igβ), BLV gp30, or the CD3γ, δ and ε chains, which also activates cytolysis, is in a chimeric receptor with a proliferation signaling domain from a Janus kinase, JAK1, JAK2, JAK3, Tyk2 or Ptk-2 or a cytokine receptor subunit. These hybrid receptors are contemplated to induce not only antigen-specific proliferation, but the activation of antigen-specific cytotoxic or helper effector function activity as well.

In yet another preferred embodiment, the present invention relates to engineered T cells expressing CPRs which already contain a chimeric effector function receptors. These dual chimera receptor-expressing T cells respond to specific antigen by activating cytolytic or helper effector function, and may respond to the same or a different antigen by proliferating as well. It is thus desirable to engineer a T cell so that it can become activated to proliferate at the disease site, as well as to kill its target, in a manner dependent only upon the presence of the appropriate antigen-expressing cell. In this preferred embodiment, the two chimeric receptors are provided to the cell as separate molecules. As an example, chimeric proliferation receptors which contain an ECD which recognizes HIV antigens are introduced into cytotoxic T cells expressing a chimeric effector function receptor which contains an ECD which recognizes the same or different HIV antigens. This will allow both the proliferation of and cytotoxic actions of the engineered cells upon contact with HIV infected cells, even in the absence of IL-2.

The chimeric construct, which encodes the chimeric protein according to this invention will be prepared in conventional ways. Since, for the most part, natural sequences may be employed, the natural genes may be isolated and manipulated, as appropriate, so as to allow for the proper joining of the various domains. Thus, one may prepare the truncated portion of the sequence by employing the polymerase chain reaction (PCR), using appropriate primers which result in deletion of the undesired portions of the gene. Alternatively, one may use primer repair, where the sequence of interest may be cloned in an appropriate host. In either case, primers may be employed which result in termini, which allow for annealing of the sequences to result in the desired open reading frame encoding the chimeric protein. Thus, the sequences may be selected to provide for restriction sites which are blunt-ended, or have complementary overlaps.

If desired, the extracellular domain may also include the transcriptional initiation region, which will allow for expression in the target host. Alternatively, one may wish to provide for a different transcriptional initiation region, which may allow for constitutive or inducible expression, depending upon the target host, the purpose for the introduction of the subject chimeric protein into such host, the level of expression desired, the nature of the target host, and the like. Thus, one may provide for expression upon differentiation or maturation of the target host, activation of the target host, or the like.

A wide variety of promoters have been described in the literature, which are constitutive or inducible, where induction may be associated with a specific cell type or a specific level of expression. Alternatively, a number of viral promoters are known which may also find use. Promoters of interest include the β-actin promoter, SV40 early and late promoters, immunoglobulin promoter, human cytomegalovirus promoter, and the Friend spleen focus-forming virus promoter. The promoters may or may not be associated with enhancers, where the enhancers may be naturally associated with the particular promoter or associated with a different promoter.

The sequence of the open reading frame may be obtained from genomic DNA, cDNA, or be synthesized, or combinations thereof. Depending upon the size of the genomic DNA and the number of introns, one may wish to use cDNA or a combination thereof. In many instances, it is found that introns stabilize the mRNA. Also, one may provide for non-coding regions which stabilize the mRNA.

A termination region will be provided 3' to the cytoplasmic domain, where the termination region may be naturally associated with the cytoplasmic domain or may be derived from a different source. For the most part, the termination regions are not critical and a wide variety of termination regions may be employed without adversely affecting expression.

The various manipulations may be carried out in vitro or may be introduced into vectors for cloning in an appropriate host, e.g., *E. coli*. Thus, after each manipulation, the resulting construct from joining of the DNA sequences may be cloned into an expression vector. The sequence may be screened by restriction analysis, sequencing, or the like to insure that it encodes the desired chimeric protein.

The chimeric construct may be introduced into the target cell in any convenient manner. Techniques include calcium phosphate or DEAE-dextran mediated DNA transfection, electroporation, protoplast fusion, liposome fusion, biolistics using DNA-coated particles, and infection, where the chimeric construct is introduced into an appropriate virus (eg retrovirus, adenovirus, adeno-associated virus, Herpes virus, Sindbis virus, papilloma virus), particularly a non-replicative form of the virus, or the like. In addition, direct injection of naked DNA or protein- or lipid-complexed DNA may also be used to introduce DNA into cells.

Once the target host has been transformed, integration will usually result. However, by appropriate choice of vectors, one may provide for episomal maintenance. A large number of vectors are known which are based on viruses, where the copy number of the virus maintained in the cell is low enough to maintain the viability of the cell. Illustrative vectors include SV40, EBV and BPV.

It is also contemplated that the introduction of the chimeric constructs of the present invention into cells may result in the transient expression of the CPRs. Such transient expression may be preferable if a short-term therapeutic effect is desired. Unstable replication or the absence of DNA replication may result, for example, from adenovirus infection or transformation with naked DNA.

Once one has established that the transformed host cell expresses the CPR of the present invention in accordance with the desired regulation and at a desired level, one may then determine whether the CPR is functional in the host cell in providing for the desired proliferation signal. One may use established methodology for measuring proliferation to verify the functional capability of the CPR. The proliferative response of cells can be measured by a variety of techniques known to those skilled in the art. For example, DNA synthesis can be measured by the incorporation of either tritiated thymidine or orotic acid. The incorporation of bromodeoxyuridine into newly synthesized DNA can be measured by immunological staining and the detection of dyes, or by ELISA (Enzyme-linked immunosorbent assay) (Doyle et al., *Cell and Tissue Culture: Laboratory Procedures*, Wiley, Chichester, England, (1994)). The mitotic index of cells can be determined by staining and microscopy, by the fraction labeled mitoses method or by FACS analysis (Doyle et al., supra, (1994); Dean, *Cell Tissue Kinet*. 13:299–308 (1980); Dean, *Cell Tissue Kinet*. 13:672–681 (1980)). The increase in cell size which accompanies progress through the cell cycle can be measure by centrifugal elutriation (Faha et al., *J Virol*. 67:2456–2465 (1993)). Increases in the number of cells may also be measured by counting the cells, with or without the addition of vital dyes. In addition, signal transduction can also be measured by the detection of phosphotyrosine, the in vitro activity of tyrosine kinases from activated cells, c-myc induction, and calcium mobilization as described in the Examples infra.

As described previously in the specific embodiments, the subject CPRs may be used to direct the proliferation of immune cells with effector function. The CPRs may be introduced into cells that already contain a chimeric receptor construct that stimulates effector function upon contact with a target inducer. The two chimeric constructs may respond to the same or different inducers. Alternatively, a hybrid CPR may be used which contains both a proliferation signaling domain and an effector function signaling domain. These cells would respond to a single target inducer by proliferating and by expressing effector function. Thus, these lymphocytes can be activated by any group of cells which contain specific membrane proteins or antigens which may be distinguished from the membrane proteins or antigens on normal cells. For example, neoplastic cells, virus-infected cells, parasiteinfected cells, or any other diseased cells would be targets for CEPR-containing lymphocytes.

Among the lymphocytes which can be used to treat human disease are cytotoxic CD8+ T cells (CTLs) which have been engineered with CEPRs containing ECDs which recognize specific antigens and can be used to kill infected cells in a variety of viral, and parasitic diseases, where the infected cells express the antigens from the pathogen. In particular, CEPR-CTLs would be particularly effective against viral diseases where transplanted autologous CTLs have shown some efficacy, such as CMV (Reusser et al, *Blood*, 78:1373–1380 (1991), Riddell et al., *Science*, 257:238–241 (1992)) or where explanted and expanded CTLs continued to have cytolytic activity against virally infected cells, such as HIV (Lieberman et al, *Aids Res. and Human Retroviruses*, 11:257–271 (1995)). These CEPRs can be constructed with ECDs which recognize the viral envelope proteins. For example, SAbs which recognize either gp120 or gp41, or the CD4 extracellular domain which recognizes gp120 can be used to engineer HIV-specific CTLs. CEPR-CTLs can also be engineered for use against other viruses, such as Hepatitis B virus, Hepatitis C virus, Kaposi's sarcoma associated Herpes virus, the Herpes Simplex viruses, Herpes Zoster virus, and papilloma viruses. Another target for the engineered CTLs are neoplastic cells which express cancer-specific neoantigens or over-express specific membrane proteins. Examples include the IL-14 receptor, CD19 and CD20 for B cell lymphoma, the Lewis Y and CEA antigens for a variety of carcinomas, the Tag72 antigen for breast and colorectal cancer, EGF-R for lung cancer, and the HER-2 protein which is often amplified in human breast and ovarian carcinomas. As an example, human Heregulin (Hrg), a protein similar in structure to Epidermal Growth Factor (EGF), has been identified as a ligand for the HER-2 protein (Holmes et al., *Science* (1992) 256:1205–1210). The extracellular domain of Hrg could be used as an ECD to form a chimeric construct of the present invention to direct T cells to kill breast carcinoma cells. CEPR-CTLs can also be used to target autoimmune cells in the treatment of autoimmune diseases such as Systemic Lupus Erythematosis (SLE), myasthenia gravis, diabetes, rheumatoid arthritis, and Grave's disease.

CD4$^+$ helper T cells (THs) engineered with CEPRs containing ECDs which recognize specific antigens can also be used to treat human disease. In particular, lymphokine production by CEPR-THs may be effective against cancer cells and mycobacterial infections, including *Mycobacterium avium*, *Mycobacterium tuberculosis* and *Mycobactium leprae*.

Chimeric proliferation receptors which do not contain effector function signaling domains may also be of use in the treatment of human disease. Various cell types containing the CPR constructs described above may be grown in an appropriate nutrient medium for expansion or may be expanded directly in the body via signaling through the CPR, depending on the cell type, and used in a variety of ways. For example, the expanded cells may be used to reconstruct existing tissue or provide new tissue in transplantation therapy. In a particular example, keratinocytes, used for replacement of skin in the case of burns, may be grown to form a continuous layer prior to application. Alternatively, the keratinocytes may be used in the case of plastic surgery to replace skin removed from the host for use at another site.

Other cell types that would be of particular interest for expansion after delivery of the CPRs of the subject invention are islets of Langerhans which may be grown and introduced into a host by capsules or other means, for the production of insulin. Retinal epithelial cells may also be expanded and injected or implanted into the subretinal space of the eye to treat visual disorders, such as macular degeneration. Immune cells, described in detail above, may be expanded ex vivo and injected into the bloodstream or elsewhere to treat immune deficiency. Myoblasts may be expanded with the present invention and injected at various sites to treat muscle wasting diseases such as Duchenne muscular dystrophy. Hepatocytes may be expanded for use in liver regeneration. Endothelial cells may also be expanded to repair blood vessels or to deliver proteins to the circulation. Nerve cells which ordinarily do not proliferate may be targets for expression by using the CPRs of present invention. In addition cells which will not proliferate in vitro, and therefore cannot be manipulated or genetically engineered may be ideal recipients of the CPRs of the present invention.

Additional types of cells that would benefit from the subject CPR constructs include cells that have genes previously introduced or simultaneously introduced with a CPR which may serve in protein production or to correct a genetic defect. Production of proteins may include growth factors, such as, erythropoietin, G-CSF, M-CSF, and GM-CSF, epidermal growth factor, platelet derived growth factor, human growth factor, transforming growth factor, etc; lymphokines, such as the interleukins; hormones, such as ACTH, somatomedin, insulin, angiotensin, etc.; coagulation factors, such as Factor VIIIC; deoxyribonuclease for treating cystic fibrosis; glucocerebrosidase for treating Gaucher's disease; normal versions of proteins associated with genetic diseases such as adenosine deaminase or the CFTR protein associated with cystic fibrosis; protective agents, such as α1-antitrypsin; regulatory proteins or enzymes associated with the production of amino acid free products, such as the expression of tyrosine hydroxylase for the production of L-dopamine, and the like.

The recipient of genetically modified allogeneic cells can be immunosuppressed to prevent the rejection of the transplanted cells. In the case of immunocompromised patients, no pretransplant therapy may be required. Another alternative source of cells to be transplanted are so-called "universal donor" cells which have been genetically engineered so that they do not express antigens of the major histocompatibility complex or molecules which function in antigen presentation.

High-titer retroviral producer lines are used to transduce the chimeric proliferation receptor constructs into autologous or allogeneic human T-cells, hematopoietic stem cells or other cells, described above through the process of retroviral mediated gene transfer as described by Lusky et al. in (1992) *Blood* 80:396. In addition to the gene encoding the chimeric proliferation receptor, additional genes may be included in the retroviral construct. These include genes such as the thymidine kinase or cytosine deaminase genes (Borrelli et al. (1988) *Proc. Natl. Acad. Sci. USA* 85:7572) which acts as a suicide gene for the marked cells if the patient is exposed to gancyclovir or 5'-fluorouracil (5FU), respectively. Thus, if the percentage of marked cells is too high, gancyclovir or 5FU may be administered to reduce the percentage of cells expressing the chimeric receptors. In addition, if the percentage of marked cells needs to be increased, the multi-drug resistance gene can be included (Sorrentino et al. (1992) *Science* 257:99) which functions as a preferential survival gene for the marked cells in the patients if the patient is administered a dose of a chemotherapeutic agent such as taxol. Therefore, the percentage of marked cells in the patients can be titrated to obtain the maximum therapeutic benefit.

In addition, high-titer adenoviral producer lines may be used to transduce the chimeric proliferation receptor constructs into autologous or allogeneic nerve cells, hematopoietic cells including stem cells, islets of Langerhans, keratinocytes, muscle cells or other cells following the methods of adenoviral mediated gene transfer as described by Finer et al. in *Blood*, 83:43–50 (1994). Similar to the procedure described above, other genes may be included in the adenoviral constructs in addition to the chimeric proliferation receptor in the recipient cell. After introduction of the construct into the cell type of interest, the cells may be expanded in an appropriate medium well know in the art and used in a variety of ways previously described.

The following examples are by way of illustration and not by way of limitation.

EXPERIMENTAL

EXAMPLE 1

Construction of CPRs comprising a ligand-receptor (CD4) extracellular clustering domain and a Janus kinase or cytokine receptor subunit proliferation signaling domain.

Expression vectors for CD4-Janus kinase and CD4-cytokine receptor subunit hybrids were created using pIK1.1F3Sal. This plasmid was made by introducing a SalI site into pIK1.1F3 (U.S. Pat. No. 5,359,046) which directs the expression CD4-ζ, a chimeric protein comprised of the human CD4 extracellular (EXT) and transmembrane (TM) domains (residues 1 to 395 of mature CD4) fused to the cytoplasmic (CYT) domain of human ζ. The SalI site was introduced by oligonucleotide-directed mutagenesis using single stranded pIK1.1F3 DNA with oligo 1 as the primer. pIK1.1F3Sal was identified by restriction analysis and its sequence confirmed by Sanger dideoxynucleotide sequencing. The creation of the SalI site results in the insertion of an Asp codon at the junction of CD4 TM and ζ CYT, and permits the replacement of ζ CYT domain with a Janus kinases or cytokine receptor subunit CYT domain with the retention of a single Asp residue at the junction. Derivatives lacking the extra Asp codon or containing other oligo- or polypeptide linkers are constructed by oligonucleotide-directed mutagenesis (Zoller and Smith, (1982) *Nucleic Acids Res,*. 10:6487–6500). In each example below, the correct expression plasmid was identified by restriction mapping and its structure confirmed by DNA sequencing.

a) Construction of CD4-mJAK1 pIKCD4-mJAK1 directs the expression of a hybrid protein consisting of the CD4 EXT and TM domains (residues 1 to 395) joined at their C-terminus to the entire mouse JAK1 Janus kinase by an Asp residue. This plasmid was constructed from three DNA fragments: 1) a vector fragment of 5.7 kb obtained by digestion of pIK1.1F3Sal with SalI and ApaI, 2) a 2.6 kb fragment encoding the N-terminus of mJAK1 obtained by digestion of pBluescriptKSmJAK1 (provided by James Ihle & Bruce Witthuhn, St Jude Children's Research Hospital, Memphis, Tenn.) with NcoI and SstI, and ligation to a SalI-NcoI adaptor consisting of oligonucleotides 2 & 3 (SEQ ID NO: 2 & 3), and 3) a 0.9 kb fragment encoding the C-terminus of mJAK1 obtained by digestion of pBluescriptKSmJAK1 with SstI and NdeI, and ligation to an NdeI-ApaI adaptor consisting of oligonucleotides 4 & 5 (SEQ ID NO: 4 & 5).

b) Construction of CD4-mJAK2 pIKCD4-mJAK2 directs the expression of a hybrid protein consisting of the CD4 EXT and TM domains (residues 1–395) joined at their C-terminus to the entire mouse JAK2 Janus kinase by an Asp residue. This plasmid was constructed in two steps. First, an intermediate plasmid was constructed from two DNA fragments: 1) a vector fragment of 5.7 kb obtained by digestion of pIK1.1F3Sal with SalI and ApaI and modification of the cohesive ends with T4 polymerase and dNTPs to create blunt ends, and 2) a 3.7 kb fragment encoding the entire mJAK2 protein obtained by digestion of pBluescriptSKmJAK2 (provided by James Ihle & Bruce Witthuhn, St Jude Children's Research Hospital, Memphis, Tenn.) with NotI and NheI and extension of the cohesive ends with T4 polymerase and dNTPs to create blunt ends. A clone with the insert in the correct orientation, having the blunted SalI and NotI sites joined, was identified and used to prepare a single-stranded DNA template. Secondly, this template was used for oligonucleotide-directed mutagenesis with oligonucleotide 6 (SEQ ID NO:6) as a primer to fuse amino acid 1 of mJAK2 in-frame to the Asp residue following the CD4 TM region. The correct expression plasmid was identified by colony hybridization using oligonucleotide 7 (SEQ ID NO:7) as a probe.

c) Construction of CD4-mJAK3 pIKCD4-mJAK3 directs the expression of a hybrid protein consisting of the CD4 EXT and TM domains (residues 1–395) joined at their C-terminus to the entire mouse JAK2 Janus kinase by an Asp residue. This plasmid was constructed from three DNA fragments: 1) a vector fragment of 5.7 kb obtained by digestion of pIK1.1F3Sal with SalI and ApaI, 2) a 1.3 kb fragment encoding the mJAK3 N-terminus obtained by digestion of pBluescriptSKmJAK3 (provided by James Ihle & Bruce Witthuhn, St Jude Children's Research Hospital, Memphis, Tenn.) with Eco47III and EcoRI, and ligation to a SalI-Eco47III adaptor consisting of oligonucleotides 8 & 9 (SEQ ID NO:8 & 9), and 3) a 2.2 kb fragment encoding the mJAK3 C-terminus obtained by digestion of pBluescriptSKmJAK3 with EcoRI and BamHI, and ligation to a BamHI-ApaI adaptor consisting of oligonucleotides 10 & 11 (SEQ ID NO:10 & 11).

d) Construction of CD4-hTyk2 pIKCD4-hTyk2 directs the expression of a hybrid protein consisting of the CD4 EXT and TM domains (residues 1–395) joined at their C-terminus to the entire human Tyk2 Janus kinase by an Asp residue. This plasmid was constructed in two steps. First, an intermediate plasmid was constructed from three DNA fragments: 1) a vector fragment of 5.7 kb obtained by digestion of pIK1.1F3Sal with SalI, extension of the cohesive end with T4 polymerase and dNTPs to create a blunt end, followed by digestion with ApaI, and 2) a 1.1 kb fragment encoding the N-terminus of hTyk2 obtained by digestion of pRCFwt (provided by Sandra Pellegrini, Institut Pasteur, Paris) with SphI, extension of the cohesive end with T4 polymerase and dNTPs, followed by digestion with SacII, and 3) a 2.6 kb fragment encoding the C-terminus of hTyk2 obtained by digestion of pRCFwt with SacII and ApaI. Secondly, a single-stranded DNA template was prepared from this intermediate plasmid and used for oligonucleotide-directed mutagenesis with oligonucleotide 12 (SEQ ID NO:12) as a primer to fuse amino acid 1 of hTyk2 in-frame to the Asp residue following the CD4 coding region. The correct expression plasmid was identified by colony hybridization using oligonucleotide 13 (SEQ ID NO:13)as a probe.

e) Construction of CD4-hJAK3 pIKCD4-hJAK3 directs the expression of a hybrid protein consisting of the CD4 EXT and TM domains (residues 1–395) joined at their C-terminus to the entire human Tyk2 Janus kinase by an Asp residue. This plasmid was constructed in two steps. First, an intermediate plasmid was constructed from three DNA fragments: 1) a vector fragment of 5.7 kb obtained by digestion of pIK1.1F3Sal with SalI and ApaI, and extension of the cohesive ends with T4 polymerase and dNTPs to create blunt ends, and 2) a 3.6 kb fragment encoding the entire hJAK3 protein obtained by digestion of pBluescriptSKhJAK3 (provided by John O'Shea, National Cancer Institute, Frederick, Md.) with EcoRI and NdeI and extension of the cohesive ends with T4 polymerase and dNTPs to create blunt ends. A clone with the insert in the correct orientation, having the blunted SalI and EcoRI sites joined, was identified and used to prepare a single-stranded DNA template. Secondly, this template was used for oligonucleotide-directed mutagenesis with oligonucleotide 14 (SEQ ID NO:14)as a primer to fuse amino acid 1 of hJAK3 in-frame to the Asp residue following the CD4 TM region. The correct expression plasmid was identified by colony hybridization using oligonucleotide 15 (SEQ ID NO:15)as a probe.

f) Construction of CD4-hIL2Rβ pIKCD4-hIL2Rβ directs the expression of a hybrid protein consisting of the CD4 EXT and TM domains (residues 1–395) joined at their C-terminus to the CYT domain of the human IL-2 receptor β subunit (residues 240–525 of the mature polypeptide) by an Asp residue. This plasmid was constructed from two DNA fragments: 1) a vector fragment of 5.7 kb obtained by digestion of pIK1.1F3Sal with ApaI, extension of the cohesive end with T4 polymerase and dNTPs to create a blunt end, followed by digestion with SalI, and 2) a 0.9 kb fragment encoding the hIL-2Rβ CYT domain obtained by digestion of a PCR-generated DNA fragment with SalI and EcoRV. The PCR-generated fragment was obtained by 1) isolating mRNA from normal human CD8-positive T cells with a FastTrack kit (Invitrogen, San Diego, Calif.), 2) using the mRNA to prepare single-stranded cDNA using a cDNA Cycle kit (Invitrogen, San Diego, Calif.) with oligonucleotide 16 (SEQ ID NO:16) as a primer, and 3) amplifying the single-stranded cDNA by PCR using oligonucleotides 17 & 18 (SEQ ID NO:17 & 18) as primers to generate a fragment which incorporates SalI and EcoRV sites at the 5' and 3' ends, respectively.

g) Construction of CD4-IL2Rγ pIKCD4-IL2Rγ directs the expression of a hybrid protein consisting of the CD4 EXT and TM domains (residues 1–395) joined at their C-terminus to the CYT domain of the human IL-2 receptor γ subunit (residues 262–347 of the mature polypeptide) by an Asp residue. This plasmid was constructed from two DNA fragments: 1) a vector fragment of 5.7 kb obtained by digestion of pIK1.1F3Sal with ApaI, extension of the cohesive end with T4 polymerase and dNTPs to create a blunt end, followed by digestion with SalI, and 2) a 0.3 kb fragment encoding the hIL-2Rγ CYT domain obtained by digestion of a PCR-generated DNA fragment with SalI and EcoRV. The PCR-generated fragment was obtained by 1) isolating a hIL-2Rγ DNA clone from a λ cDNA library made from activated human T cells (Clontech, Palo Alto, Calif.) using oligonucleotides 19 & 20 (SEQ ID NO:19 & 20)as probes, 2) subcloning an EcoRI fragment containing the hIL-2Rγ CYT domain (residues 268–347), 3) using the subclone DNA to carry out PCR with oligos 21 and 22 as primers to generate a fragment in which the codons for hIL-2Rγ residues 262–267 were recreated, the EcoRI site was removed, and in which SalI and EcoRV sites were incorporated at the 5' and 3' ends, respectively.

EXAMPLE 2

CPRs containing an antibody extracellular clustering domain and a Janus kinase or cytokine receptor subunit proliferation signaling domain.

Expression vectors for SAb-Janus kinase and SAb-cytokine receptor subunit hybrids are created by replacing the CD4 EXT domain in CD4-Janus kinase and CD4-cytokine receptor subunit hybrids (examples 1a to 1g) with the EXT domain of F15γ2, a single-chain antibody-ζ chimeric receptor, contained in plasmid pRT43.2F15γ2. F15γ2 is comprised of (from N- to C-terminus) of: 1) the signal sequence and $V_K$ domain of human anti-HIV gp41 MAb 98.6 (residues 1–107 of the mature protein), 2) a 14 amino acid peptide linker (Gly-Ser-Thr-Ser-Gly-Ser-Gly-Lys-Ser-Ser-Glu-Gly-Lys-Gly), 3) the $V_H$ domain of MAb 98.6 (residues 1–113 of the mature protein), 4) the hinge, CH2 and CH3 domains of the human IgG2 heavy chain constant region (residues 226 to 477), 5) the 18 residue human IgG3 M1 membrane hinge, 6) the CD4 TM domain (residues 372–395), and 7) the ζ CYT domain (residues 31–142). The presence of the IgG2 heavy chain constant domain allows such SAb-Janus kinase and SAb-cytokine receptor subunit constructs to form disulfide-linked dimers. Derivatives which lack the constant domain, and thus do not dimerize, are made by oligonucleotide directed mutagenesis. Other derivatives lacking the Asp codon or containing other oligo- or polypeptide linkers at the junction of CD4 TM and the CYT domain of the Janus kinase or cytokine receptor subunit are constructed by oligonucleotide directed mutagenesis. In each example, the correct expression plasmid is identified by restriction mapping and its structure confirmed by DNA sequencing.

a) Construction of SAb-mJAK1 pIKSAb-mJAK1 directs the expression of a hybrid protein consisting of the SAb EXT and CD4 TM domains of F15γ2 joined at their C-terminus to the entire mouse JAK1 Janus kinase by an Asp residue. This plasmid is constructed from three DNA fragments: 1) a vector fragment of 4.3 kb obtained by digestion of the expression plasmid pIK1.1 with EcoRI and ApaI, 2) a fragment of 1.6 kb encoding the SAb EXT domain and part of the CD4 TM domain, obtained by digestion of pRT43.2F15γ2 with EcoRI and NgoMI, and 3) a 3.7 kb fragment encoding the remainder of the CD4 TM domain and the entire mJAK1 protein, obtained by digestion of pIKCD4-mJAK1 with NgoMI and ApaI.

b) Construction of SAb-mJAK2 pIKSAb-mJAK2 directs the expression of a hybrid protein consisting of the SAb EXT and CD4 TM domains of F15γ2 joined at their C-terminus to the entire mouse JAK2 Janus kinase by an Asp residue. This plasmid is constructed from three DNA fragments: 1) a vector fragment of 7.6 kb encoding the entire mJAK2 protein, obtained by digestion of pIKCD4-mJAK2 with SphI and SalI, 2) a fragment of 0.7 kb encoding the N-terminal portion of the SAb EXT domain, obtained by digestion of pIKSAb-mJAK1 with SphI and BamHI, and 3) a fragment of 1.0 kb encoding the remainder of the SAb EXT domain and the CD4 TM domain, obtained by digestion of pIKSAb-mJAK1 with BamHI and SalI.

c) Construction of SAb-mJAK3 pIKSAb-mJAK3 directs the expression of a hybrid protein consisting of the SAb EXT and CD4 TM domains of F15γ2 joined at their C-terminus to the entire mouse JAK2 Janus kinase by an Asp residue. This plasmid is constructed from three DNA fragments: 1) a vector fragment of 7.7 kb encoding the entire mJAK3 protein, obtained by digestion of pIKCD4-mJAK3 with SphI and SalI, 2) a fragment of 0.7 kb encoding the N-terminal portion of the SAb EXT domain, obtained by digestion of pIKSAb-mJAK1 with SphI and BamHI, and 3) a fragment of 1.0 kb encoding the remainder of the SAb EXT domain and the CD4 TM domain, obtained by digestion of DIKSAb-mJAK1 with BamHI and SalI.

d) Construction of SAb-hTyk2 pIKSAb-hTyk2 directs the expression of a hybrid protein consisting of the SAb EXT and CD4 TM domains of F15γ2 joined at their C-terminus to the entire human Tyk2 Janus kinase by an Asp residue. This plasmid is constructed from three DNA fragments: 1) a vector fragment of 7.5 kb encoding the C-terminus of hTyk2, obtained by digestion of pIKCD4-hTyk2 with EcoRI and BspEI, 2) a fragment of 1.6 kb encoding the SAb EXT domain and a portion of the CD4 TM domain, obtained by digestion of pRT43.2F15γ2 with EcoRI and NgoMI, and 3) a fragment of 0.4 kb encoding the remainder of the CD4 TM domain and the N-terminus of the hTyk2 protein, obtained by digestion of pIKCD4-hTyk2 with NgoMI and BspEI.

e) Construction of Sab-CD4-hJAK3 pIKSAb-hJAK3 directs the expression of a hybrid protein consisting of the SAb EXT and CD4 TM domains of F15γ2 joined at their C-terminus to the entire human JAK3 Janus kinase by an Asp residue. This plasmid is constructed from three DNA fragments: 1) a vector fragment of 7.7 kb encoding the entire mJAK3 protein, obtained by digestion of pIKCD4-hJAK3 with SphI and SalI, 2) a fragment of 0.7 kb encoding the N-terminal portion of the SAb EXT domain, obtained by digestion of pIKSAb-mJAK1 with SphI and BamHI, and 3) a fragment of 1.0 kb encoding the remainder of the SAb EXT domain and the CD4 TM domain, obtained by digestion of pIKSAb-mJAK1 with BamHI and SalI.

f) Construction of SAb-IL2Rβ pIKSAb-hIL2Rβ directs the expression of a hybrid protein consisting of the SAb EXT and CD4 TM domains of F15γ2 joined at their C-terminus to the human IL2Rβ CYT domain by an Asp residue. This plasmid is constructed from three DNA fragments: 1) a vector fragment of 5.0 kb encoding the IL-2Rβ CYT domain, obtained by digestion of pIKCD4-hIL2Rβ with SphI and SalI, 2) a fragment of 0.7 kb encoding the N-terminal portion of the SAb EXT domain, obtained by digestion of pIKSAb-mJAK1 with SphI and BamHI, and 3) a fragment of 1.0 kb encoding the remainder of the SAb EXT domain and the CD4 TM domain, obtained by digestion of pIKSAb-mJAK1 with BamHI and SalI.

g) Construction of SAb-IL2Rγ pIKSAb-hIL2Rγ directs the expression of a hybrid protein consisting of the SAb EXT and CD4 TM domains of F15γ2 joined at their C-terminus to the human IL2Rγ CYT domain by an Asp residue. This plasmid is constructed from three DNA fragments: 1) a vector fragment of 4.4 kb encoding the IL-2Rγ CYT domain, obtained by digestion of pIKCD4-hIL2Rγ with SphI and SalI, 2) a fragment of 0.7 kb encoding the N-terminal portion of the SAb EXT domain, obtained by digestion of pIKSAb-mJAK1 with SphI and BamHI, and 3) a fragment of 1.0 kb encoding the remainder of the SAb EXT domain and the CD4 TM domain, obtained by digestion of pIKSAb-mJAK1 with BamHI and SalI.

EXAMPLE 3

CPRs comprising a ligand-receptor (CD4) extracellular clustering domain, a ζ family signalling domain and a Janus kinase or cytokine receptor subunit proliferation signaling domain.

This class of chimeric receptors were created by the insertion of a ζ family CYT signaling domain (e.g. ζ, η, the FcRε γ subunit, B29, and CD3 γ, δ and ε subunits) into a CPR between the TM domain and proliferation signaling (Janus kinase or cytokine receptor subunit) domain. These chimeric receptors were constructed from pIK1.1F3SalB, an intermediate plasmid based on pIK1.1F3 (which encodes CD4-ζ). A SalI site was introduced into the CD4-ζ coding sequence between the last amino acid and stop codon by oligonucleotide-directed mutagenesis using pIK1.1F3 single-stranded DNA with oligonucleotide 23 (SEQ ID NO:23) as a primer and oligonucleotide 24 (SEQ ID NO:24) to identify the correct clone by colony hybridization. This results in the addition of 2 residues (Val-Asp) at the carboxyl terminus of CD4-ζ. The proliferation signaling domain of a Janus kinase or cytokine receptor subunit was then joined at the C-terminus of CD4-ζ using the unique SalI site which adds a Val-Asp dipeptide at the junction. Derivatives lacking the Val-Asp dipeptide or containing other oligo- or polypeptide linkers are constructed by oligonucleotide-directed mutagenesis. A similar strategy is used to create CPRs containing a ζ family signaling domain at the C-terminus of the chimeric protein (e.g., CD4-Janus kinase-ζ and CD4-cytokine receptor subunit-ζ) by inserting the ζ family CYT domain after the proliferation signalling CYT domain.

a) Construction of CD4-ζ-mJAK1 pIKCD4-ζ-mJAK1 directs the expression of a hybrid protein consisting of the CD4 EXT and TM domains (residues 1 to 395) and ζ CYT domain joined at their C-terminus to the entire mouse JAK1 Janus kinase by a Val-Asp dipeptide. This plasmid was constructed from two DNA fragments: 1) a vector fragment of 7.7 kb encoding the entire mJAK1 protein, obtained by digestion of pIKCD4-mJAK1 with SphI and SalI, 2) a 1.8 kb fragment encoding the CD4 EXT and TM domains and the ζ CYT domain, obtained by digestion of pIK1.1F3SalB with SphI and SalI.

b) Construction of CD4-ζ-mJAK2 pIKCD4-ζ-mJAK2 directs the expression of a hybrid protein consisting of the CD4 EXT and TM domains (residues 1 to 395) and ζ CYT domain joined at their C-terminus to the entire mouse JAK2 Janus kinase by a Val-Asp dipeptide. This plasmid was constructed from two DNA fragments: 1) a vector fragment of 7.6 kb encoding the entire mJAK2 protein, obtained by digestion of pIKCD4-mJAK2 with SphI and SalI, 2) a 1.8 kb fragment encoding the CD4 EXT and TM domains and the ζ CYT domain, obtained by digestion of pIK1.1F3SalB with SphI and SalI.

c) Construction of CD4-ζ-mJAK3 pIKCD4-ζ-mJAK3 directs the expression of a hybrid protein consisting of the CD4 EXT and TM domains (residues 1 to 395) and ζ CYT domain joined at their C-terminus to the entire mouse JAK3 Janus kinase by a Val-Asp dipeptide. This plasmid was constructed from two DNA fragments: 1) a vector fragment of 7.7 kb encoding the entire mJAK3 protein, obtained by digestion of pIKCD4-mJAK3 with SphI and SalI, 2) a 1.8 kb fragment encoding the CD4 EXT and TM domains and the ζ CYT domain, obtained by digestion of pIK1.1F3SalB with SphI and SalI.

d) Construction of CD4-ζ-hTyk2 pIKCD4-ζ-hTyk2 directs the expression of a hybrid protein consisting of the CD4 EXT and TM domains (residues 1 to 395) and ζ CYT domain joined at their C-terminus to the entire human Tyk2 Janus kinase by a Val-Asp dipeptide. This plasmid was constructed from three DNA fragments: 1) a vector fragment of 7.5 kb encoding the C-terminus of hTyk2, obtained by digestion of pIKCD4-hTyk2 with EcoRI and BspEI, 2) a 1.7 kb fragment encoding the CD4 EXT and TM domains and the ζ CYT domain, obtained by digestion of pIK1.1F3SalB with EcoRI and SalI, and 3) a 0.3 kb fragment encoding the N-terminus of hTyk2, obtained by digestion of pIK1.1F3SalB with SalI and BspEI.

e) Construction of CD4-ζ-hJAK3 pIKCD4-ζ-hJAK3 directs the expression of a hybrid protein consisting of the CD4 EXT and TM domains (residues 1 to 395) and ζ CYT domain joined at their C-terminus to the entire human JAK3 Janus kinase by a Val-Asp dipeptide. This plasmid was constructed from two DNA fragments: 1) a vector fragment of 7.7 kb encoding the entire hJAK3 protein, obtained by digestion of pIKCD4-hJAK3 with SphI and SalI, 2) a 1.8 kb fragment encoding the CD4 EXT and TM domains and the ζ CYT domain, obtained by digestion of pIK1.1F3SalB with SphI and SalI.

f) Construction of CD4-ζ-hIL2Rβ pIKCD4-ζ-hIL2Rβ directs the expression of a hybrid protein consisting of the CD4 EXT and TM domains (residues 1 to 395) and ζ CYT domain joined at their C-terminus to the human IL2Rβ CYT domain subunit by a Val-Asp dipeptide. This plasmid is constructed from two DNA fragments: 1) a vector fragment of 5.0 kb encoding the hIL2Rβ CYT domain, obtained by digestion of pIKCD4-hIL2Rβ with SphI and SalI, 2) a 1.8 kb fragment encoding the CD4 EXT and TM domains and the ζ CYT domain, obtained by digestion of pIK1.1F3SalB with SphI and SalI.

g) Construction of CD4-ζ-hIL2Rγ pIKCD4-ζ-hIL2Rγ directs the expression of a hybrid protein consisting of the CD4 EXT and TM domains (residues 1 to 395) and ζ CYT domain joined at their C-terminus to the human IL2Rγ CYT domain by a Val-Asp dipeptide. This plasmid is constructed from two DNA fragments: 1) a vector fragment of 4.4 kb encoding the hIL2Rγ CYT domain, obtained by digestion of pIKCD4-hIL2Rβ with SphI and SalI, 2) a 1.8 kb fragment encoding the CD4 EXT and TM domains and the ζ CYT domain, obtained by digestion of pIK1.1F3SalB with SphI and SalI.

EXAMPLE 4

CPRs containing an antibody extracellular clustering domain, a ζ family signaling domain and a Janus kinase or cytokine receptor subunit proliferation signaling domain.

This class of chimeric receptors are created by the insertion of a ζ family CYT signaling domain (e.g. ζ, η, the FcRε γ subunit, B29, and CD3 γ, δ and ε subunits) into an antibody-based CPR between the TM domain and proliferation signaling (Janus kinase or cytokine receptor subunit) domain. These chimeric receptors are constructed from CD4-ζ-Janus kinase and CD4-ζ-cytokine receptor subunit CPRs, by substituting an antibody-based EXT clustering domain for the CD4 EXT domain. The proliferation signalling domain of a Janus kinase or cytokine receptor subunit is joined at the C-terminus of SAb-ζ by a Val-Asp dipeptide. Derivatives lacking the Val-Asp dipeptide or containing other oligo- or polypeptide linkers are constructed by oligonucleotide-directed mutagenesis. A similar strategy is used to create CPRs containing a ζ family signaling domain at the C-terminus of the chimeric protein (e.g., SAb-Janus kinase-ζ and SAb-cytokine receptor subunit-ζ) by inserting the ζ family CYT domain after the proliferation signalling CYT domain.

a) Construction of SAb-ζ-mJAK1 pIKSAb-ζ-mJAK1 directs the expression of a hybrid protein consisting of the 98.6 SAb EXT, CD4 TM and ζ CYT domain joined at their C-terminus to the entire mouse JAK1 Janus kinase by a Val-Asp dipeptide. This plasmid is constructed from three DNA fragments: 1) a vector fragment of 4.3 kb obtained by digestion of the expression plasmid pIK1.1 with EcoRI and ApaI, 2) a fragment of 1.6 kb encoding the SAb EXT domain and part of the CD4 TM domain, obtained by digestion of pRT43.2F15γ2 with EcoRI and NgoMI, and 3) a 4.0 kb fragment encoding the remainder of the CD4 TM domain, the ζ CYT domain and the entire mJAK1 protein, obtained by digestion of pIKCD4-ζ-mJAK1 with NgoMI and ApaI.

b) Construction of SAb-ζ-mJAK2 pIKSAb-ζ-mJAK2 directs the expression of a hybrid protein consisting of the 98.6 SAb EXT, CD4 TM and ζ CYT domain joined at their C-terminus to the entire mouse JAK2 Janus kinase by a Val-Asp dipeptide. This plasmid is constructed from three DNA fragments: 1) a vector fragment of 7.6 kb encoding the entire mJAK2 protein, obtained by digestion of pIKCD4-mJAK2 with SphI and SalI, 2) a fragment of 0.7 kb encoding the N-terminal portion of the SAb EXT domain, obtained by digestion of pIKSAb-ζ-mJAK1 with SphI and BamHI, and 3) a fragment of 1.4 kb encoding the remainder of the SAb EXT domain, the CD4 TM domain and the ζ CYT domain, obtained by digestion of pIKSAb-ζ-mJAK1 with BamHI and SalI.

c) Construction of SAb-ζ-mJAK3 pIKSAb-ζ-mJAK3 directs the expression of a hybrid protein consisting of the 98.6 SAb EXT, CD4 TM and ζ CYT domain joined at their C-terminus to the entire mouse JAK3 Janus kinase by a Val-Asp dipeptide. This plasmid is constructed from three DNA fragments: 1) a vector fragment of 7.7 kb encoding the entire mJAK3 protein, obtained by digestion of pIKCD4-mJAK3 with SphI and SalI, 2) a fragment of 0.7 kb encoding the N-terminal portion of the SAb EXT domain, obtained by digestion of pIKSAb-ζ-mJAK1 with SphI and BamHI, and 3) a fragment of 1.4 kb encoding the remainder of the SAb EXT domain, the CD4 TM domain and the ζ CYT domain, obtained by digestion of pIKSAb-ζ-mJAK1 with BamHI and SalI.

d) Construction of SAb-ζ-hTyk2 pIKSAb-ζ-hTyk2 directs the expression of a hybrid protein consisting of the 98.6 EXT, CD4 TM and ζ CYT domain joined at their C-terminus to the entire human Tyk2 Janus kinase by a Val-Asp dipeptide. This plasmid is constructed from three DNA fragments: 1) a vector fragment of 7.5 kb encoding the C-terminus of hTyk2, obtained by digestion of pIKCD4-hTyk2 with EcoRI and BspEI, 2) a fragment of 1.6 kb encoding the SAb EXT domain and a portion of the CD4 TM domain, obtained by digestion of pIKSAb-ζ-mJAK1 with EcoRI and NgoMI, and 3) a fragment of 1.6 kb encoding the remainder of the CD4 TM domain, the ζ CYT domain and the N-terminus of the hTyk2 protein, obtained by digestion of pIKCD4-ζ-hTyk2 with NgoMI and BspEI.

e) Construction of SAb-ζ-hJAK3 pIKCD4-ζ-hJAK3 directs the expression of a hybrid protein consisting of the 98.6 EXT, CD4 TM and ζ CYT domain joined at their C-terminus to the entire human JAK3 Janus kinase by a Val-Asp dipeptide. This plasmid is constructed from three DNA fragments: 1) a vector fragment of 7.7 kb encoding the entire hJAK3 protein, obtained by digestion of pIKCD4-hJAK3 with SphI and SalI, 2) a fragment of 0.7 kb encoding the N-terminal portion of the SAb EXT domain, obtained by digestion of pIKSAb-ζ-mJAK1 with SphI and BamHI, and 3) a fragment of 1.4 kb encoding the remainder of the SAb EXT domain, the CD4 TM domain and the ζ CYT domain, obtained by digestion of pIKSAb-ζ-mJAK1 with BamHI and SalI.

f) Construction of SAb-ζ-hIL2Rβ pIKSAb-ζ-hIL2Rβ directs the expression of a hybrid protein consisting of the 98.6 EXT, CD4 TM and ζ CYT domain joined at their C-terminus to the human IL2Rβ CYT domain by a Val-Asp dipeptide. This plasmid is constructed from three DNA fragments: 1) a vector fragment of 5.0 kb encoding the hIL2Rβ CYT domain, obtained by digestion of pIKCD4-hIL2Rβ with SphI and SalI, 2) a fragment of 0.7 kb encoding the N-terminal portion of the SAb EXT domain, obtained by digestion of pIKSAb-ζ-mJAK1 with SphI and BamHI, and 3) a fragment of 1.4 kb encoding the remainder of the SAb EXT domain, the CD4 TM domain and the ζ CYT domain, obtained by digestion of pIKSAb-ζ-mJAK1 with BamHI and SalI.

g) Construction of SAb-ζ-hIL2Rγ pIKSAb-ζ-hIL2Rγ directs the expression of a hybrid protein consisting of the 98.6 EXT, CD4 TM and ζ CYT domain joined at their C-terminus to the human IL2Rγ CYT domain by a Val-Asp dipeptide. This plasmid is constructed from three DNA fragments: 1) a vector fragment of 4.4 kb encoding the hIL2Rγ CYT domain, obtained by digestion of pIKCD4-hIL2Rγ with SphI and SalI, 2) a fragment of 0.7 kb encoding the N-terminal portion of the SAb EXT domain, obtained by digestion of pIKSAb-ζ-mJAK1 with SphI and BamHI, and 3) a fragment of 1.4 kb encoding the remainder of the SAb EXT domain, the CD4 TM domain and the ζ CYT domain, obtained by digestion of pIKSAb-ζ-mJAK1 with BamHI and SalI.

EXAMPLE 5

CPRs containing a ligand-receptor (CD4) extracellular clustering domain, a Syk family kinase signaling domain and a Janus kinase or a cytokine receptor subunit proliferation signaling domain.

This class of chimeric receptors are created by the insertion of a Syk family kinase (e.g., Syk and ZAP-70) into a CPR between the TM domain and proliferation signaling (Janus kinase or cytokine receptor subunit) domain. These chimeric receptors are constructed from CD4-ζ-Janus kinase or CD4-ζ-cytokine receptor subunit CPRs, by replacing the ζ family CYT domain with the entire Syk family polypeptide. CPRs based on the Syk kinase are made from the intermediate plasmid pIK1.1CD4-Syk which directs the expression of a hybrid protein consisting of the CD4 EXT and TM domains joined to the entire human Syk polypeptide by a Glu residue. This plasmid is constructed from two fragments: 1) a vector fragment of 5.7 kb encoding the CD4 EXT and TM domains, obtained by digestion of pIK1.1F3Sal with ApaI, extension of the cohesive end to a blunt end with T4 DNA polymerase and dNTPs, followed by digestion with SalI, and 2) a 1.8 kb PCR fragment encoding human Syk kinase, generated using ψHM3-Syk (provided by Edward Clark, U. of Washington, Seattle, Wash.) as a PCR template with oligonucleotides 25 & 26 (SEQ ID NO:25 & 26) as primers to introduce XhoI and EcoRV sites at the 5' and 3' ends, respectively, followed by digestion with XhoI and EcoRV. The Janus kinase or cytokine receptor subunit is then joined at the C-terminus of CD4-Syk using the unique SalI site which adds a Val-Asp dipeptide at the junction. Derivatives lacking the Val-Asp dipeptide or containing other oligo- or polypeptide linkers are constructed by oligonucleotide-directed mutagenesis. A similar strategy is used to create CPRs containing a Syk family kinase at the C-terminus of the chimeric protein (e.g., CD4-Janus kinase-ζ and CD4-cytokine receptor subunit-ζ) by inserting the Syk family kinase after the proliferation signalling CYT domain.

a) Construction of CD4-Syk-mJAK1 pIKCD4-Syk-mJAK1 directs the expression of a hybrid protein consisting of the CD4 EXT and TM domains (residues 1 to 395) and the entire Syk protein joined at their C-terminus to the entire mouse JAK1 Janus kinase by a Val-Asp dipeptide. This plasmid is constructed from two DNA fragments: 1) a vector fragment of 7.7 kb encoding the entire mJAK1 protein, obtained by digestion of pIKCD4-mJAK1 with SphI and SalI, and 2) a 3.3 kb fragment encoding the CD4 EXT and TM domains and the entire Syk protein, obtained by digestion of pIK1.1CD4-Syk with SphI and SalI.

b) Construction of CD4-Syk-mJAK2 pIKCD4-Syk-mJAK2 directs the expression of a hybrid protein consisting of the CD4 EXT and TM domains (residues 1 to 395) and the entire Syk protein joined at their C-terminus to the entire mouse JAK2 Janus kinase by a Val-Asp dipeptide. This plasmid is constructed from two DNA fragments: 1) a vector fragment of 7.6 kb encoding the entire mJAK2 protein, obtained by digestion of pIKCD4-mJAK2 with SphI and SalI, and 2) a 3.3 kb fragment encoding the CD4 EXT and TM domains and the entire Syk protein, obtained by digestion of pIK1.1CD4-Syk with SphI and SalI.

c) Construction of CD4-Syk-mJAK3 pIKCD4-Syk-mJAK3 directs the expression of a hybrid protein consisting of the CD4 EXT and TM domains (residues 1 to 395) and the entire Syk protein joined at their C-terminus to the entire mouse JAK3 Janus kinase by a Val-Asp dipeptide. This plasmid is constructed from two DNA fragments: 1) a vector fragment of 7.7 kb encoding the entire mJAK3 protein, obtained by digestion of pIKCD4-mJAK3 with SphI and SalI, and 2) a 3.3 kb fragment encoding the CD4 EXT and TM domains and the entire Syk protein, obtained by digestion of pIK1.1CD4-Syk with SphI and SalI.

d) Construction of CD4-Syk-hTyk2 pIKCD4-Syk-hTyk2 directs the expression of a hybrid protein consisting of the CD4 EXT and TM domains (residues 1 to 395) and the entire Syk protein joined at their C-terminus to the entire human Tyk2 Janus kinase by a Val-Asp dipeptide. This plasmid is constructed from three DNA fragments: 1) a vector fragment of 7.5 kb encoding the C-terminus of hTyk2, obtained by digestion of pIKCD4-hTyk2 with EcoRI and BspEI, 2) a 3.3 kb fragment encoding the CD4 EXT and TM domains and the entire Syk protein, obtained by digestion of pIK1.1CD4-Syk with EcoRI and SalI, and 3) an 0.3 kb fragment encoding the N-terminus of hTyk2, obtained by digestion of pIK1.1F3SalB with SalI and BspEI.

e) Construction of CD4-Syk-hJAK3 pIKCD4-Syk-hJAK3 directs the expression of a hybrid protein consisting of the CD4 EXT and TM domains (residues 1 to 395) and the entire Syk protein joined at their C-terminus to the entire human JAK3 Janus kinase by a Val-Asp dipeptide. This plasmid is constructed from two DNA fragments: 1) a vector fragment of 7.7 kb encoding the entire hJAK3 protein, obtained by digestion of pIKCD4-hJAK3 with SphI and SalI, and 2) a 3.3 kb fragment encoding the CD4 EXT and TM domains and the entire Syk protein, obtained by digestion of pIK1.1CD4-Syk with SphI and SalI.

f) Construction of CD4-Syk-hIL2Rβ pIKCD4-Syk-hIL2Rβ directs the expression of a hybrid protein consisting of the CD4 EXT and TM domains (residues 1 to 395) and the entire Syk protein joined at their C-terminus to the human IL2Rβ CYT domain by a Val-Asp dipeptide. This plasmid is constructed from two DNA fragments: 1) a vector fragment of 5.0 kb encoding the hIL2Rβ CYT domain, obtained by digestion of pIKCD4-hIL2Rβ with SphI and SalI, 2) a 3.3 kb fragment encoding the CD4 EXT and TM domains and the entire Syk protein, obtained by digestion of pIK1.1CD4-Syk with SphI and SalI.

g) Construction of CD4-Syk-hIL2Rγ pIKCD4-Syk-hIL2Rγ directs the expression of a hybrid protein consisting of the CD4 EXT and TM domains (residues 1 to 395) and the entire Syk protein joined at their C-terminus to the human IL2Rγ CYT domain by a Val-Asp dipeptide. This plasmid is constructed from two DNA fragments: 1) a vector fragment of 4.4 kb encoding the hIL2Rβ CYT domain, obtained by digestion of pIKCD4-hIL2Rβ with SphI and SalI, 2) a 3.3 kb fragment encoding the CD4 EXT and TM domains and the entire Syk protein, obtained by digestion of pIK1.1CD4-Syk with SphI and SalI.

EXAMPLE 6

CPRs containing an antibody extracellular clustering domain, and a Syk family kinase signaling domain and Janus kinase & cytokine receptor subunit proliferation signaling domain This class of chimeric receptors are created by the insertion of a Syk family kinase (e.g. Syk and ZAP-70) into an antibody-based CPR between the TM domain and proliferation signaling (Janus kinase or cytokine receptor subunit) domain. These chimeric receptors are constructed from CD4-Syk-Janus kinase and CD4-Syk-cytokine receptor subunit CPRs, by substituting an antibody-based EXT clustering domain for the CD4 EXT domain. The proliferation signaling domain of a Janus kinase or cytokine receptor subunit is joined at the C-terminus of SAb-Syk by a Val-Asp dipeptide. Derivatives lacking the Val-Asp dipeptide or containing other oligo- or polypeptide linkers are constructed by oligonucleotide-directed mutagenesis. A similar strategy is used to create CPRs containing a Syk family kinase at the C-terminus of the chimeric protein (e.g., SAb-Janus kinase-Syk kinase and SAb-cytokine receptor subunit-Syk kinase) by inserting the Syk family kinase after the proliferation signalling CYT domain.

a) Construction of SAb-Syk-mJAK1 pIKSAb-Syk-mJAK1 directs the expression of a hybrid protein consisting of the 98.6 SAb EXT, CD4 TM and the entire Syk protein joined at their C-terminus to the entire mouse JAK1 Janus kinase by a Val-Asp dipeptide. This plasmid is constructed from three DNA fragments: 1) a vector fragment of 7.7 kb encoding the entire mJAK1 protein, obtained by digestion of pIKCD4-mJAK1 with SphI and SalI, 2) a fragment of 1.7 kb encoding the SAb EXT domain and part of the CD4 TM domain, obtained by digestion of pIKSAb-mJAK1 with SphI and NgoMI, and 3) a 2.0 kb fragment encoding the remainder of the CD4 TM domain and the entire Syk protein, obtained by digestion of pIKCD4-Syk-mJAK1 with NgoMI and SalI.

b) Construction of SAb-Syk-mJAK2 pIKSAb-Syk-mJAK2 directs the expression of a hybrid protein consisting of the 98.6 SAb EXT, CD4 TM and Syk CYT domain joined at their C-terminus to the entire mouse JAK2 Janus kinase by a Val-Asp dipeptide. This plasmid is constructed from three DNA fragments: 1) a vector fragment of 7.6 kb encoding the entire mJAK2 protein, obtained by digestion of pIKCD4-mJAK2 with SphI and SalI, 2) a fragment of 0.7 kb encoding the N-terminal portion of the SAb EXT domain, obtained by digestion of pIKSAb-ζ-mJAK1 with SphI and BamHI, and 3) a fragment of 3.0 kb encoding the remainder of the SAb EXT domain, the CD4 TM domain and the entire Syk protein, obtained by digestion of pIKSAb-Syk-mJAK1 with BamHI and SalI.

c) Construction of SAb-Syk-mJAK3 pIKSAb-Syk-mJAK3 directs the expression of a hybrid protein consisting of the 98.6 SAb EXT, CD4 TM and Syk CYT domain joined at their C-terminus to the entire mouse JAK3 Janus kinase by a Val-Asp dipeptide. This plasmid is constructed from three DNA fragments: 1) a vector fragment of 7.7 kb encoding the entire mJAK3 protein, obtained by digestion of pIKCD4-mJAK3 with SphI and SalI, 2) a fragment of 0.7 kb encoding the N-terminal portion of the SAb EXT domain, obtained by digestion of pIKSAb-ζ-mJAK1 with SphI and BamHI, and 3) a fragment of 3.0 kb encoding the remainder of the SAb EXT domain, the CD4 TM domain and the entire Syk protein, obtained by digestion of pIKSAb-Syk-mJAK1 with BamHI and SalI.

d) Construction of SAb-Syk-hTyk2 pIKSAb-Syk-hTyk2 directs the expression of a hybrid protein consisting of the 98.6 EXT, CD4 TM and Syk CYT domain joined at their C-terminus to the entire human Tyk2 Janus kinase by a Val-Asp dipeptide. This plasmid is constructed from three DNA fragments: 1) a vector fragment of 7.5 kb encoding the C-terminus of hTyk2, obtained by digestion of pIKCD4-hTyk2 with EcoRI and BspEI, 2) a 1.6 kb fragment encoding the SAb EXT and part of the CD4 TM domain, obtained by digestion of pIKSAb-mJAK1 with EcoRI and NgoMI, and 3) an 2.3 kb fragment encoding the remainder of the CD4 TM domain, the entire human Syk protein and the N-terminus of hTyk2, obtained by digestion of pIKCD4-Syk-hTyk2 with NgoMI and BspEI.

e) Construction of SAb-Syk-hJAK3 pIKCD4-Syk-hJAK3 directs the expression of a hybrid protein consisting of the 98.6 EXT, CD4 TM and Syk CYT domain joined at their C-terminus to the entire human JAK3 Janus kinase by a Val-Asp dipeptide. This plasmid is constructed from three DNA fragments: 1) a vector fragment of 7.7 kb encoding the entire hJAK3 protein, obtained by digestion of pIKCD4-hJAK3 with SphI and SalI, 2) a fragment of 0.7 kb encoding the N-terminal portion of the SAb EXT domain, obtained by digestion of pIKSAb-ζ-mJAK1 with SphI and BamHI, and 3) a fragment of 3.0 kb encoding the remainder of the SAb EXT domain, the CD4 TM domain and the entire Syk protein, obtained by digestion of pIKSAb-Syk-mJAK1 with BamHI and SalI.

f) Construction of SAb-Syk-hIL2Rβ pIKSAb-Syk-hIL2Rβ directs the expression of a hybrid protein consisting of the 98.6 EXT, CD4 TM and Syk CYT domain joined at their C-terminus to the human IL2Rβ CYT domain by a Val-Asp dipeptide. This plasmid is constructed from three DNA fragments: 1) a vector fragment of 5.0 kb encoding the hIL2Rβ CYT domain, obtained by digestion of pIKCD4-hIL2Rβ with SphI and SalI, 2) a fragment of 0.7 kb encoding the N-terminal portion of the SAb EXT domain, obtained by digestion of pIKSAb-ζ-mJAK1 with SphI and BamHI, and 3) a fragment of 3.0 kb encoding the remainder of the SAb EXT domain, the CD4 TM domain and the entire Syk protein, obtained by digestion of pIKSAb-Syk-mJAK1 with BamHI and SalI.

g) Construction of SAb-Syk-hIL2Rγ pIKSAb-Syk-hIL2Rγ directs the expression of a hybrid protein consisting of the 98.6 EXT, CD4 TM and Syk CYT domain joined at their C-terminus to the human IL2Rγ CYT domain by a Val-Asp dipeptide. This plasmid is constructed from three DNA fragments: 1) a vector fragment of 4.4 kb encoding the hIL2Rγ CYT domain, obtained by digestion of pIKCD4-hIL2Rγ with SphI and SalI, 2) a fragment of 0.7 kb encoding the N-terminal portion of the SAb EXT domain, obtained by digestion of pIKSAb-ζ-mJAK1 with SphI and BamHI, and 3) a fragment of 3.0 kb encoding the remainder of the SAb EXT domain, the CD4 TM domain and the entire Syk protein, obtained by digestion of pIKSAb-Syk-mJAK1 with BamHI and SalI.

EXAMPLE 7

CPRs containing an intracellular clustering domain: and a Janus kinase or cytokine receptor subunit proliferation signaling domain Expression vectors for FKBP-Janus kinase and FKBP-cytokine receptor subunit hybrids are created by replacing the CD4 EXT and TM domains in CD4-Janus kinase and CD4-cytokine receptor subunit hybrids with an $(FKBP)_3$ cassette consisting of three repeats of an FKBP module, each of which contains residues 2–108 of FKBP12, the human FK506 binding protein (Standaert et al. (1990) *Nature* 346:671–674). The first FKBP module is preceded by an initiator Met codon, then a two amino linker, Val-Glu. This same Val-Glu dipeptide is found between module 1 & 2 and between modules 2 & 3. The last module is followed by a Val-Asp dipeptide which links it to the first codon of the proliferation signalling domain. Other derivatives lacking the Val-Asp dipeptide or containing other oligo- or polypeptide linkers at the junction of the (FKBP)3 cassette and the Janus kinase or cytokine receptor subunit CYT domain are constructed by oligonucleotide-directed mutagenesis. Still other derivatives of $(FKBP)_3$ lacking the Val-Glu dipeptide linkers or containing other oligo- or polypeptide linkers are constructed by oligonucleotide-directed mutagenesis. The $(FKBP)_3$ cassette is constructed in two steps. First, a plasmid containing the FKBP module, pFKBP, is constructed from two DNA fragment: 1) a vector fragment of 2.9 kb, obtained by digestion of pBluescriptSK (Strategene, La Jolla, Calif.) with XhoI and SalI, and treatment with calf intestine alkaline phosphatase, and 2) a DNA fragment of 0.3 kb encoding the FKBP module, obtained by PCR and digested with XhoI and SalI. The PCR product is prepared using as a template oligo dT-primed first-strand cDNA made from activated T cell mRNA (as described in Example 1) and oligos nucleotides 27 and 28 (SEQ ID NOS: 27 & 28) as the PCR primers. DNA sequence analysis is employed to confirm the correct structure of the module. Secondly, plasmid $pBSK(FKBP)_3$ containing the $(FKBP)_3$ cassette is constructed from three fragments: 1) a vector fragment of 2.9 kb, obtained by digestion of pBluescriptSK with EcoRI and SalI, 2) a DNA fragment of 1.0 kb encoding $(FKBP)_3$, obtained by extensive self-ligation and subsequent digestion with XhoI and SalI of an 0.3 kb fragment encoding the FKBP module, obtained by digestion of pFKBP with XhoI and SalI, and 3) an EcoRI-XhoI adapter composed of oligos nucleotides 29 and 30 (SEQ ID NOS. 29 & 30).

a) Construction of FKBP-mJAK1 pIKFKBP-mJAK1 directs the expression of a hybrid protein consisting of the $(FKBP)_3$ coding sequence of pBSK $(FKBP)_3$ joined at its C-terminus to the entire mouse JAK1 Janus kinase by a Val-Asp dipeptide. This plasmid is constructed from three DNA fragments: 1) a vector fragment of 4.3 kb, obtained by digestion of the expression plasmid pIK1.1 with EcoRI and ApaI, 2) a fragment of 1.0 kb encoding the $(FKBP)_3$ cassette, obtained by digestion of $pBSK(FKBP)_3$ with EcoRI and SalI, and 3) a 3.6 kb fragment encoding the entire mJAK1 protein, obtained by digestion of pIKCD4-mJAK1 with SalI and ApaI.

b) Construction of FKBP-mJAK2 pIKFKBP-mJAK2 directs the expression of a hybrid protein consisting of the $(FKBP)_3$ coding sequence of pBSK $(FKBP)_3$ joined at its C-terminus to the entire mouse JAK2 Janus kinase by a Val-Asp dipeptide. This plasmid is constructed from two DNA fragments: 1) a vector fragment of 7.6 kb encoding the entire mJAK2 protein, obtained by digestion of pIKCD4-mJAK2 with SphI and SalI, and 2) a fragment of 1.1 kb encoding the $(FKBP)_3$ cassette, obtained by digestion of pIKFKBP-mJAK1 with SphI and SalI.

c) Construction of FKBP-mJAK3 pIKFKBP-mJAK3 directs the expression of a hybrid protein consisting of the $(FKBP)_3$ coding sequence of pBSK (FKBP)₃ joined at its C-terminus to the entire mouse JAK3 Janus kinase by a Val-Asp dipeptide. This plasmid is constructed from two DNA fragments: 1) a vector fragment of 7.7 kb encoding the entire mJAK3 protein, obtained by digestion of pIKCD4-mJAK3 with SphI and SalI, and 2) a fragment of 1.1 kb encoding the (FKBP)₃ cassette, obtained by digestion of pIKFKBP-mJAK1 with SphI and SalI.

d) Construction of FKBP-hTyk2 pIKFKBP-hTyk2 directs the expression of a hybrid protein consisting of the (FKBP)₃ coding sequence of pBSK (FKBP)₃ joined at its C-terminus to the entire human Tyk2 Janus kinase by a Val-Asp dipeptide. This plasmid is constructed from three DNA fragments: 1) a vector fragment of 7.5 kb encoding the C-terminus of hTyk2, obtained by digestion of pIKCD4-hTyk2 with EcoRI and BspEI, 2) a fragment of 1.0 kb encoding the (FKBP)₃ cassette, obtained by digestion of pIKFKBP-mJAK1 with EcoRI and SalI, and 3) a fragment of 0.3 kb encoding the N-terminus of the hTyk2 protein, obtained by digestion of pIKCD4-hTyk2 with SalI and BspEI.

e) Construction of FKBP-hJAK3 pIKFKBP-hJAK3 directs the expression of a hybrid protein consisting of the (FKBP)₃ coding sequence of pBSK (FKBP)₃ joined at its C-terminus to the entire human JAK3 Janus kinase by a Val-Asp dipeptide. This plasmid is constructed from two DNA fragments: 1) a vector fragment of 7.7 kb encoding the entire hJAK3 protein, obtained by digestion of pIKCD4-hJAK3 with SphI and SalI, and 2) a fragment of 1.1 kb encoding the (FKBP)₃ cassette, obtained by digestion of pIKFKBP-mJAK1 with SphI and SalI.

f) Construction of FKBP-IL2Rβ pIKFKBP-hIL2Rβ directs the expression of a hybrid protein consisting of the (FKBP)₃ coding sequence of pBSK (FKBP)₃ joined at its C-terminus to the human IL2Rβ CYT domain by a Val-Asp dipeptide. This plasmid is constructed from two DNA fragments: 1) a vector fragment of 5.0 kb encoding the hIL2Rβ CYT domain, obtained by digestion of pIKCD4-hIL2Rβ with SphI and SalI, and 2) a fragment of 1.1 kb encoding the (FKBP)₃ cassette, obtained by digestion of pIKFKBP-mJAK1 with SphI and SalI.

g) Construction of FKBP-IL2Rγ pIKFKBP-hIL2Rγ directs the expression of a hybrid protein consisting of the (FKBP)₃ coding sequence of pBSK (FKBP)₃ joined at its C-terminus to the human IL2Rγ CYT domain by a Val-Asp dipeptide. This plasmid is constructed from two DNA fragments: 1) a vector fragment of 4.4 kb encoding the hIL2Rγ CYT domain, obtained by digestion of pIKCD4-hIL2Rγ with SphI and SalI, and 2) a fragment of 1.1 kb encoding the (FKBP)₃ cassette, obtained by digestion of pIKFKBP-mJAK1 with SphI and SalI.

EXAMPLE 8

CPRs containing a ligand-receptor (CD4) extracellular clustering domain; an intracellular clustering domain; and a Janus kinase or cytokine receptor subunit proliferation signaling domain This class of chimeric receptors are created by the insertion of an (FKBP)₃ cassette into a CD4-Janus kinase or CD4-cytokine receptor subunit CPR between the TM domain and proliferation signaling domain. These chimeric receptors are constructed from pIKCD4-(FKBP)₃, an intermediate plasmid based on pIK1.1F3Sal. The proliferation signaling domain of a Janus kinase or cytokine receptor subunit is then joined at the C-terminus of CD4-(FKBP)₃ using the unique SalI site which adds a Val-Asp dipeptide at the junction. Derivatives lacking the Val-Asp dipeptide or containing other oligo- or polypeptide linkers are constructed by oligonucleotide-directed mutagenesis. A similar strategy is used to create CPRs containing an (FKBP)₃ cassette at the C-terminus of the chimeric protein (e.g., CD4-Janus kinase-FKBP and CD4-cytokine receptor subunit-FKBP) by inserting the (FKBP)₃ cassette after the proliferation signalling CYT domain. pIKCD4-(FKBP)₃ is constructed from two DNA fragments: 1) a vector fragment of 5.8 kb encoding the CD4 EXT and TM domains, obtained by digestion of pIK1.1F3Sal with SalI followed by treatment with calf intestine alkaline phosphatase, and 2) a 1.0 kb fragment encoding the (FKBP)₃ cassette, obtained by digestion of pBSK(FKBP)₃ with XhoI and SalI. Clones with the (FKBP)₃ cassette in the correct in-frame orientation are confirmed by restriction mapping.

a) Construction of CD4-FKBP-mJAK1 pIKCD4-FKBP-mJAK1 directs the expression of a hybrid protein consisting of the CD4-(FKBP)₃ coding sequence joined at its C-terminus to the entire mouse JAK1 Janus kinase by a Val-Asp dipeptide. This plasmid is constructed from two DNA fragments: 1) a vector fragment of 7.7 kb encoding the entire mJAK1, obtained by digestion of pIKCD4-mJAK1 with SphI and SalI, and 2) a fragment of 2.3 kb encoding CD4-(FKBP)₃, obtained by digestion of pIKCD4-(FKBP)₃ with SphI and SalI.

b) Construction of CD4-FKBP-mJAK2 pIKCD4-FKBP-mJAK2 directs the expression of a hybrid protein consisting of the CD4-(FKBP)₃ coding sequence joined at its C-terminus to the entire mouse JAK2 Janus kinase by a Val-Asp dipeptide. This plasmid is constructed from two DNA fragments: 1) a vector fragment of 7.6 kb encoding the entire mJAK2, obtained by digestion of pIKCD4-mJAK2 with SphI and SalI, and 2) a fragment of 2.3 kb encoding CD4-(FKBP)₃, obtained by digestion of pIKCD4-(FKBP)₃ with SphI and SalI.

c) Construction of CD4-FKBP-mJAX3 pIKCD4-FKBP-mJAK3 directs the expression of a hybrid protein consisting of the CD4-(FKBP)₃ coding sequence joined at its C-terminus to the entire mouse JAK3 Janus kinase by a Val-Asp dipeptide. This plasmid is constructed from two DNA fragments: 1) a vector fragment of 7.7 kb encoding the entire mJAK3, obtained by digestion of pIKCD4-mJAK3 with SphI and SalI, and 2) a fragment of 2.3 kb encoding CD4-(FKBP)₃, obtained by digestion of pIKCD4-(FKBP)₃ with SphI and SalI.

d) Construction of CD4-FKBP-hTyk2 pIKCD4-FKBP-hTyk2 directs the expression of a hybrid protein consisting of the CD4-(FKBP)₃ coding sequence joined at its C-terminus to the entire human Tyk2 Janus kinase by a Val-Asp dipeptide. This plasmid is constructed from three DNA fragments: 1) a vector fragment of 7.5 kb encoding the C-terminus of hTyk2, obtained by digestion of pIKCD4-hTyk2 with EcoRI and BspEI, 2) a fragment of 2.3 kb encoding the CD4-(FKBP)₃ cassette, obtained by digestion of pIKCD4-(FKBP)₃ with EcoRI and SalI, and 3) a fragment of 0.3 kb encoding the N-terminus of the hTyk2 protein, obtained by digestion of pIKCD4-hTyk2 with SalI and BspEI.

e) Construction of CD4-FKBP-hJAK3 pIKCD4-FKBP-hJAK3 directs the expression of a hybrid protein consisting of the CD4-(FKBP)₃ coding sequence joined at its C-terminus to the entire human JAK3 Janus kinase by a Val-Asp dipeptide. This plasmid is constructed from two DNA fragments: 1) a vector fragment of 7.7 kb encoding the entire hJAK3, obtained by digestion of pIKCD4-hJAK3 with SphI and SalI, and 2) a fragment of 2.3 kb encoding CD4-(FKBP)₃, obtained by digestion of pIKCD4-(FKBP)₃ with SphI and SalI.

f) Construction of CD4-FKBP-IL2Rβ pIKCD4-FKBP-hIL2Rβ directs the expression of a hybrid protein consisting of the CD4-(FKBP)$_3$ coding sequence joined at its C-terminus to the hIL2Rβ CYT domain by a Val-Asp dipeptide. This plasmid is constructed from two DNA fragments: 1) a vector fragment of 5.0 kb encoding the hIL2Rβ CYT domain, obtained by digestion of pIKCD4-hIL2Rβ with SphI and SalI, and 2) a fragment of 2.3 kb encoding CD4-(FKBP)$_3$, obtained by digestion of pIKCD4-(FKBP)$_3$ with SphI and SalI.

g) Construction of CD4-FKBP-IL2Rγ pIKCD4-FKBP-hIL2Rγ directs the expression of a hybrid protein consisting of the CD4-(FKBP)$_3$ coding sequence joined at its C-terminus to the hIL2Rγ CYT domain by a Val-Asp dipeptide. This plasmid is constructed from two DNA fragments: 1) a vector fragment of 4.4 kb encoding the entire mJAKl, obtained by digestion of pIKCD4-hIL2Rγ with SphI and SalI, and 2) a fragment of 2.3 kb encoding CD4-(FKBP)$_3$, obtained by digestion of pIKCD4-(FKBP)$_3$ with SphI and SalI.

EXAMPLE 9

CPRs containing antibody extracellular clustering domain, an intracellular clustering domain: and a Janus kinase or cytokine receptor subunit proliferation domain This class of chimeric receptors are created by the insertion of an (FKBP)$_3$ cassette into a SAb-Janus kinase or SAb-cytokine receptor subunit CPR between the TM domain and proliferation signalling domain. The proliferation signalling domain of a Janus kinase or cytokine receptor subunit is joined at the C-terminus of SAb-(FKBP)$_3$ using the SalI site which adds a Val-Asp dipeptide at the junction. Derivatives lacking the Val-Asp dipeptide or containing other oligo- or polypeptide linkers are constructed by oligonucleotide-directed mutagenesis. A similar strategy is used to create CPRs containing an (FKBP)$_3$ cassette at the C-terminus of the chimeric protein (e.g., SAb-Janus kinase-FKBP and SAb-cytokine receptor subunit-FKBP) by inserting the (FKBP)$_3$ cassette after the proliferation signalling CYT domain.

a) Construction of SAb-FKBP-mJAK1 pIKSAb-FKBP-mJAK1 directs the expression of a hybrid protein consisting of the SAb EXT domain, CD4 TM domain and (FKBP)$_3$ cassette joined to the entire mouse JAK1 Janus kinase by a Val-Asp dipeptide. This plasmid is constructed from three DNA fragments: 1) a vector fragment of 7.7 kb encoding the entire mJAK1 protein, obtained by digestion of pIKCD4-mJAK1 with SphI and SalI, 2) a fragment of 17 kb encoding the SAb EXT domain and a portion of the CD4 TM domain, obtained by digestion of pIKSAb-mJAK1 with SphI and NgoMI, and 3) a 1.0 kb fragment encoding the remainder of the CD4 TM domain and the (FKBP)$_3$ cassette, obtained by digestion of pIKCD4-(FKBP)$_3$ with NgoMI and SalI.

b) Construction of SAb-FKBP-mJAK2 pIKSAb-FKBP-mJAK2 directs the expression of a hybrid protein consisting of the SAb EXT domain, CD4 TM domain and (FKBP)$_3$ cassette joined to the entire mouse JAK2 Janus kinase by a Val-Asp dipeptide. This plasmid is constructed from three DNA fragments: 1) a vector fragment of 7.6 kb encoding the entire mJAK2 protein, obtained by digestion of pIKCD4-mJAK2 with SphI and SalI, 2) a fragment of 0.7 kb encoding the N-terminal portion of the SAb EXT domain, obtained by digestion of pIKSAb-mJAK1 with SphI and BamHI, and 3) a fragment of 2.0 kb encoding the remainder of the SAb EXT domain, the CD4 TM domain and the (FKBP)$_3$ cassette, obtained by digestion of pIKSAb-FKBP-mJAK1 with BamHI and SalI.

c) Construction of SAb-FKBP-mJAK3 pIKSAb-FKBP-mJAK3 directs the expression of a hybrid protein consisting of the SAb EXT domain, CD4 TM domain and (FKBP)$_3$ cassette joined to the entire mouse JAK3 Janus kinase by a Val-Asp dipeptide. This plasmid is constructed from three DNA fragments: 1) a vector fragment of 7.7 kb encoding the entire mJAK3 protein, obtained by digestion of pIKCD4-mJAK3 with SphI and SalI, 2) a fragment of 0.7 kb encoding the N-terminal portion of the SAb EXT domain, obtained by digestion of pIKSAb-mJAK1 with SphI and BamHI, and 3) a fragment of 2.0 kb encoding the remainder of the SAb EXT domain, the CD4 TM domain and the (FKBP)$_3$ cassette, obtained by digestion of pIKSAb-FKBP-mJAK1 with BamHI and SalI.

d) Construction of SAb-FKBP-hTyk2 pIKSAb-FKBP-hTyk2 directs the expression of a hybrid protein consisting of the SAb EXT domain, CD4 TM domain and (FKBP)$_3$ cassette joined to the entire human Tyk2 Janus kinase by a Val-Asp dipeptide. This plasmid is constructed from three DNA fragments: 1) a vector fragment of 7.5 kb encoding the C-terminus of the Tyk2 protein, obtained by digestion of pIKCD4-hTyk2 with EcoRI and BspEI, 2) a fragment of 1.6 kb encoding the SAb EXT domain and a portion of the CD4 TM domain, obtained by digestion of pIKSAb-mJAK1 with EcoRI and NgoMI, and 3) a fragment of 1.5 kb encoding the remainder of the CD4 TM domain, the (FKBP)$_3$ cassette and the N-terminus of hTyk2, obtained by digestion of pIKCD4-FKBP-hTyk2 with NgoMI and BspEI.

e) Construction of SAb-FKBP-hJAK3 pIKSAb-FKBP-hJAK3 directs the expression of a hybrid protein consisting of the SAb EXT domain, CD4 TM domain and (FKBP)$_3$ cassette joined to the entire human JAK3 Janus kinase by a Val-Asp dipeptide. This plasmid is constructed from three DNA fragments: 1) a vector fragment of 7.7 kb encoding the entire mJAK2 protein, obtained by digestion of pIKCD4-hJAK3 with SphI and SalI, 2) a fragment of 0.7 kb encoding the N-terminal portion of the SAb EXT domain, obtained by digestion of pIKSAb-mJAK1 with SphI and BamHI, and 3) a fragment of 2.0 kb encoding the remainder of the SAb EXT domain, the CD4 TM domain and the (FKBP)$_3$ cassette, obtained by digestion of pIKSAb-FKBP-mJAK1 with BamHI and SalI.

f) Construction of SAb-FKBP-IL2Rβ pIKSAb-FKBP-hIL2Rβ directs the expression of a hybrid protein consisting of the SAb EXT domain, CD4 TM domain and (FKBP)$_3$ cassette joined to the hIL2Rβ CYT domain by a Val-Asp dipeptide. This plasmid is constructed from three DNA fragments: 1) a vector fragment of 5.0 kb encoding the hIL2Rβ CYT domain, obtained by digestion of pIKCD4-hIL2Rβ with SphI and SalI, 2) a fragment of 0.7 kb encoding the N-terminal portion of the SAb EXT domain, obtained by digestion of pIKSAb-mJAK1 with SphI and BamHI, and 3) a fragment of 2.0 kb encoding the remainder of the SAb EXT domain, the CD4 TM domain and the (FKBP)$_3$ cassette, obtained by digestion of pIKSAb-FKBP-mJAK1 with BamHI and SalI.

g) Construction of SAb-FKBP-IL2Rγ pIKSAb-FKBP-hIL2Rγ directs the expression of a hybrid protein consisting of the SAb EXT domain, CD4 TM domain and (FKBP)$_3$ cassette joined to the hIL2Rγ CYT domain by a Val-Asp dipeptide. This plasmid is constructed from three DNA fragments: 1) a vector fragment of 4.4 kb encoding the hIL2Rγ CYT domain, obtained by digestion of pIKCD4-hIL2Rγ with SphI and SalI, 2) a fragment of 0.7 kb encoding the N-terminal portion of the SAb EXT domain, obtained by digestion of pIKSAb-mJAK1 with SphI and BamHI, and 3) a fragment of 2.0 kb encoding the remainder of the SAb EXT domain, the CD4 TM domain and the (FKBP)$_3$ cassette, obtained by digestion of pIKSAb-FKBP-mJAK1 with BamHI and SalI.

EXAMPLE 10
Expression of CPRs

To determine whether CPR polypeptides can be expressed and properly folded, each construct was initially transfected into a model mammalian cell, the human 293 embryonic kidney cell line (ATCC CRL1573). Following transfection, the expression of each construct was evaluated by radioimmunoprecipitation, and its transport to the cell surface (for CPRs comprising a ligand-receptor or antibody EXT domain) was evaluated by fluorescent-activated cell sorting (FACS) analysis.

a) Transfection of human 293 cells with CPR expression vectors CPRs were constructed in pIK mammalian expression plasmids as described and transfected into human 293 cells. 293 cells were grown in complete DMEM (JRH Biosciences, Lenexa, Kans.), 1 g/l glucose, 10% donor calf serum (JRH Biosciences) and passaged at 1:10 split ratio every 3 days. Twenty-four hours prior to transfection, 293 cells were plated at $5 \times 10^5$ cells per 10 cm plate. Ten micrograms of plasmid DNA was transfected onto a 10 cm dish of 293 cells by the calcium phosphate coprecipitation method (Wigler et al. (1979) *Cell* 16:777). Twenty-four hours after transfection, the cells were fed with fresh complete DMEM media. The expression of CPRs was evaluated by FACS analysis and radioimmunoprecipitation at 48 hours post-transfection.

b) FACS analysis of CPR expression in 293 cells

Transfected 293 cells were rinsed once with PBS and incubated in 150 mM NaCl, 40 mM Tris-HCl pH7.5, 1 mM EDTA solution for 5 minutes at room temperature. Cells were collected from plates, centrifuged and resuspended in PBS/1% FCS. Approximately $1 \times 10^6$ cells/sample were stained directly with saturating concentrations of a fluorescein (FITC)-conjugated anti-CD4 monoclonal antibody (MAb) (Becton Dickinson Immunocytometry Systems, San Jose, Calif.). Mouse FITC-IgG1 and PE-IgG2a were used as negative control MAbs. 293 cells transfected with 10 μg of PIKF3, which expresses CD4-ζ, were used as a positive control. All FACS analyses were performed in a FACScan (Becton Dickinson) as previously described (Weiss and Stobo, (1984) *J. Exp. Med.*, 160:1284–1299). FACS analysis of cells transfected with CPRs containing a CD4 EXT clustering domain demonstrated that up to 50% of cells were stained positive with the anti-CD4 MAb (FIG. 3(A)–(L)). 293 cells transfected with CPR constructs containing a SAb EXT clustering domain are evaluated for expression of the CPR by staining with a fluorescein-conjugated mouse anti-human Ig MAb, using isotype-matched mouse FITC-IgG as a negative control. 293 cells transfected with CPR constructs containing an intracellular clustering domain (e.g., FKBP, glucocorticoid receptor) are evaluated for expression of the CPR by first partially permeabilizing the cells with 70% methanol for 30 seconds on ice, followed by staining the cells with FITC-conjugated anti-PSD antibody (see Example 10C). An isotype matched mouse FITC-IgG is used as a negative control.

c) Radioimmunoprecipitation of CPRs expressed in 293 cells

Figure 4:
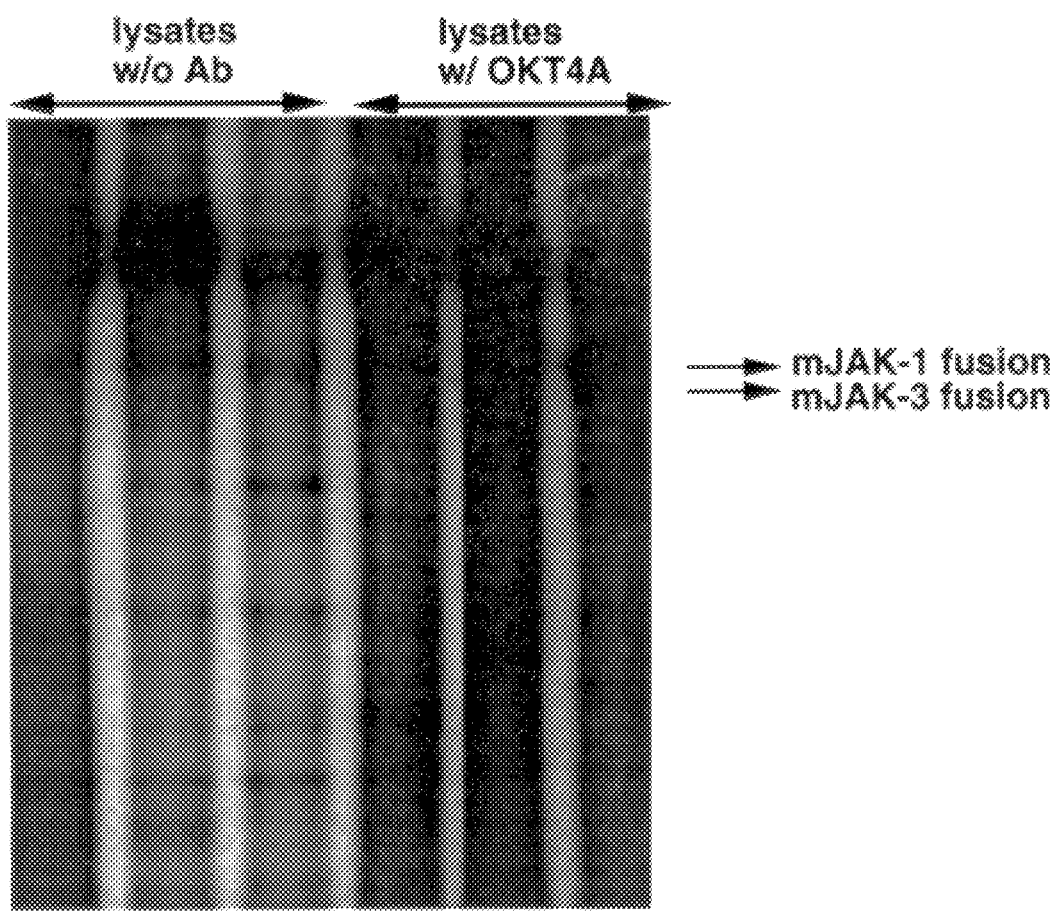
FIG. 4 is an autoradiogram of immunoprecipitations of lysates from 293 cells transfected with CD4-Janus kinase constructs as described in Example 10(C). (Lanes 1 & 4: Mock-transfected; Lanes 2 & 5: CD4-mJAK1; Lanes 3 & 6: CD4-mJAK3; Lanes 1–3: no antibody and Lanes 4–6: OKT4A antibody.)

Transfected 293 cells were rinsed once with RPMI medium lacking methionine. Cells were cultured for additional 8 hours in 2 μl of methionine-deficient RPMI supplemented with 200 μCi [$^{35}$S]-methionine (1160 C/mmol, ICN Biomedicals, Inc., Irvine, Calif.). The labelled cells were lysed in RIPA buffer (50 mM Tris, 150 mM NaCl, 1% Triton-X 100, 0.5% deoxycholate, 0.1% sodium dodecyl sulfate (SDS)). For immunoprecipitation, cell lysates were precleared with 10 μl Pansorbin (Calbiochem, La Jolla, Calif.) and incubated with either OKT4A (anti-CD4) (Ortho Diagnostic Systems, Raritan, N.J.), polyclonal anti-mouse/human JAK1 (UBI, Lake Placid, N.Y.), polyclonal anti-mouse JAK2 (UBI), or polyclonal anti-mouse JAK3 (UBI), at 4° C. for 1 hour. Ten microliters of Pansorbin was then added to the lysates to precipitate the antibody-bound antigen. Immunoprecipitates were washed three times in RIPA buffer, boiled in SDS sample buffer (50 mM Tris-HCl, pH 6.8, 100 mM DTT, 2% SDS, 0.1% bromophenol blue, 10% glycerol) and analyzed by 8% SDS-polyacrylamide gel electrophoresis (SDS-PAGE). Gels were fixed in 20% methanol/10% acetic acid and soaked in Enlightening solution (NEN Research Products, Boston, Mass.) for 15 min, dried and subjected to autoradiography. SDS-PAGE analysis revealed the expression of CPRs in 293 cells of the expected molecular mass (FIG. 4)

EXAMPLE 11
Biochemical and biological properties of CPRs expressed in human CD8$^+$ T cells a) Construction of CPR-expressing retroviral vectors Sequences encoding the CPRs CD4-mJAK1, CD4-ζ-mJAK1, CD4-mJAK3, CD4-ζ-mJAK3, CD4-hTyk2, and CD4-ζ-hTyk2 were inserted between the EcoRI and ApaI sites in pIK1.1, and were subsequently excised and inserted between analogous EcoRI and ApaI sites of pRT43.2F3, described in U.S. patent application Ser. No. 08/258,152 incorporated herein in its entirety by reference, generally as two subfragments to avoid internal EcoRI or ApaI sites within the CPR constructs. One skilled in the art can readily devise schemes for producing retroviral vectors containing other CPRs.

b) Infection of human CD8$^+$ T cells with CPR-expressing retroviral vectors

Human CD8$^+$ T lymphocytes were isolated from peripheral blood lymphocytes (PBL) obtained from healthy donors by purification with the CEPRATE LC system (CellPro, Inc., Bothell, Wash.), followed by negative selection against CD4$^+$ cells using a T-25 MicroCELLector (AIS, Inc., Santa Clara, Calif.). The final purified cell population contained greater than 98% CD8$^+$ cells according to FACS analysis. Immediately after purification, cells were stimulated for 24 hours with an equal number of γ-irradiated autologous PBMCs in AIM-V media (GibcoBRL, Grand Island, N.Y.) containing 10 ng/μl of OKT3 MAb and 100 units of human IL-2 (Chiron Corp., Emeryville, Calif.). Cells were then washed free of OKT3 and cultured in AR media (50% AIM-V, 50% RPMI, 4 mM Glutamine, 20 mM Hepes, 1 mM Na-Pyruvate, non-essential amino acids, and 100 units human IL-2) supplemented with 5% heat inactivated human AB plasma (Sigma, St. Louis, Mo.). Retrovirus was prepared in the TIN-4 cell line derived from thymidine kinase-expressing human 293 cells. For the transduction of human CD8$^+$ cells, TIN-4 cells were seeded at $5 \times 10^5$ cell/plate in 6-well plates (Corning Glass, Corning, N.Y.) in complete DMEM medium 48 hours prior to transfection. Ten micrograms of CPR construct in the retroviral vector pRT43.2 were transfected per plate in the absence or presence of packaging plasmids by the calcium phosphate coprecipitation method. Following transfection, 1.5 ml of fresh AR medium containing 100 units/ml of human IL-2 was added to each well of the plate. Three hours later, $5 \times 10^5$ of CD8$^+$ T cells in AR media containing 100 units/ml of human IL-2 and 2 μg/ml of polybrene were added to each well of the plate. CD8+ T cells were removed from the 6-well plates 24 hours later and then transduced a second time by the same procedure. Newly transduced CD8+ T cells were maintained in AR media.

c) FACS analysis of CPR expression in human CD8+ T cells

At various times following transduction, CD8+ T cells were harvested and washed with PBS/1% FCS. Approximately 1×10$^6$ CD8+ T cells were stained with specific antibodies for FACS analysis as described in Example 10B. As shown in Table 1, chimeric proliferation receptors can be expressed on the surface of CD8+ T cells.

TABLE I

| Transduction | % Positive in CD8+ T Cells |
|---|---|
| Mock | 1.7 |
| CD4-ζ | 18.2 |
| CD4-mJAK1 | 4.0 |
| CD4-mJAK3 | 3.8 |
| CD4-hTyk2 | 7.5 |
| CD4-ζ-hTyk2 | 4.6 | d) Immunoprecipitation analysis of CPR expression in human CD8+ T cells

At various times following transduction, human CD8+ T cells are harvested and placed in methionine-depleted AR media supplemented with 200 μCi [$^{35}$S]-methionine (1160 Ci/mmol, ICN Biomedicals, Inc.). Cells are lysed in RIPA buffer, precleared with 10 μl Pansorbin (except cells expresssed SAb-containing CPRs) (Calbiochem, La Jolla, Calif.), and then incubated with either OKT4A (Ortho Diagnostic Systems), polyclonal anti-mouse/human JAK1 (UBI, Lake Placid, N.Y.), polyclonal anti-mouse JAK2 (UBI), or polyclonal anti-mouse JAK3 (UBI) at 4° C. for 1 hour. Ten microliters of Pansorbin are then added to the lysates to precipitate the antibody-bound antigen. The immunoprecipitates are washed three times in RIPA buffer, boiled in SDS sample buffer and analyzed by 7.5% SDS-polyacrylamide gel electrophoresis. Gels are fixed in 20% methanol/ 10% acetic acid and then soaked in Enlightening solution (NEN Research Products, Boston, Mass.) for 15 minutes, dried and subjected to autoradiography. SDS-PAGE analysis reveals the molecular mass of CPRs expressed in human CD8+ T cells.

e) Analysis of CPR-expressing human CD8+ T cells for phosphotyrosine content

To assess the phosphotyrosine content of human CD8+ T cells expressing CPRs, 5×10$^6$ cells are lysed in protein phosphotyrosine lysis buffer (1% Nonidet P-40, 150 mM NaCl, 10 mM Tris-HCl, pH 7.5, 1 mM phenylmethylsulfonyl fluoride, 10 μg/ml aprotinin, 10 μg/ml pepstatin, 100 uM orthovanadate) at 4° C. for 15 min, and immunoprecipitated with either OKT4A, anti-human/mouse JAK1, anti-mouse JAK2, anti-mouse JAK3, anti-human JAK3 or anti-human-Tyk2. The immunoprecipitates are separated by 7.5% SDS-PAGE and the proteins are transferred electrophoretically to a nitrocellulose membrane in transfer buffer (20 mM Tris, 150 mM glycine, 20% methanol, 0.2% SDS) at 50 volts for 4 hours. Membranes are blocked in TBST (10 mM Tris-HCl, pH 8, 150 mM NaCl, 0.05% Tween-20) containing 1% BSA and then incubated with primary anti-phosphotyrosine antibody 4G10 (UBI). The membrane is developed using the enhanced chemiluminescence (ECL) detection system (Amersham, Arlington Height, Ill.).

f) Analysis of CPR-expressing human CD8+ T cell lysates for in vitro kinase activity As JAK kinases have the ability to be autophosphorylated, human CD8+ T cells expressing CPRs are evaluated for their CPR-associated tyrosine kinase activity. Immunoprecipitates prepared from CPR-transduced human CD8+ T cells using either OKT4A, anti-human Fc Mab, anti-human/mouse JAK1, anti-mouse JAK2, anti-mouse JAK3, anti-human JAK3 or anti-human-Tyk2, as described above, are washed three times with protein tyrosine lysis buffer and once with kinase buffer (10 mM MnCl$_2$, 50 mM Tris-HCl, pH 7.5). Kinase reactions are performed in 25 μl of kinase buffer containing 10 μCi γ-[32-P]ATP (95,000 Ci/mmole, Amersham). Following a 5 minute incubation at 25° C., the reactions are terminated by addition of equal volume of 2×SDS sample buffer, boiled for 5 minutes and subjected to SDS-PAGE. The gel is fixed, treated with 1M KOH at 55° C. for 1 hour to remove serine/threonine phosphorylated residues, refixed, dried and subjected to autoradiography.

g) Proliferative response of CPR-expressing human CD8+ T cells

To evaluate the ability of CPR-expressing CD8+ T cells to proliferate in an antigen-driven or inducer molecule-driven fashion, cells are first rested by serum starvation for 16 hours. Cells are then placed in culture dishes coated with saturating concentrations of either OKT4A, anti-human Fc Mab, gp120, gp160-expressing cells, gp41/gp120-expressing cells, HIV-1 infected cells or FK1012. After 5 to 48 hours, the total cell numbers is determined by counting, following staining with trypan blue/PBS. The cell number is compared with the original cell number, and the cell numbers obtained after starvation with or without stimulation with media containing human serum. In addition, analysis of cellular proliferation is carried out by measuring radioactive thymidine incorporation. Cells are starved for 16 hours and aliquoted in quadruplicate into microliter plates at 5×10$^4$ cells/well. The plates are either coated with OKT4A or anti-gp120, gp160-expressing cells, gp41/gp120-expressing cells, HIV-1 infected cells or FK1012. Cells are cultured under these conditions for up to three days, and thymidine incorporation is measured in a liquid scintillation counter after pulsing the cells for the last 8 hours with 1 μCi/well of [$^3$H]thymidine (NEN Corp, Boston, Mass.).

h) C-myc induction in CPR-expressing human CD8+ T cells

To evaluate the induction of the c-myc proto-oncogene in CPR-expressing CD8+ T cells stimulated with a specific antigen or inducer molecule, mRNA is prepared using a Fast Track mRNA isolation kit (Invitrogen, San Diego, Calif.). Two micrograms of mRNA is denatured with formaldehyde/ formamide and run on a 1% agarose-formaldehyde gel as described (Sambrook et al, *Molecular Cloning*, Cold Spring Harbor Laboratory Press, 1989). The mRNA is transferred overnight by capillary action to a nitrocellulose membrane (Schleicher and Schuell, Keene, N.H.) in 10× SSC buffer. The membrane is hybridized overnight with a c-myc probe at 65° C. in 6× SSC, 0.5% sodium dodecyl sulfate and 100 mg/ml of denatured herring sperm DNA, washed in 0.2× SSC and subjected to autoradiography. The c-myc probe is prepared with a 1 kb ClaI-EcoRI fragment obtained from pMyc6514 (Battey et al, *Cell* 34, 779–787, 1983) which contains the third exon of human c-myc. Radiolabelling of the probe is carried by random priming with *E. coli* DNA polymerase, dNTPs and α [32-P]dCTP (3000 Ci/mmole, Amersham, Arlington Heights, Ill.) as described (Sambrook et al). As a control for the amount of RNA loaded on the gel, the nitrocellulose membrane is rehybridized with a 1.3 kb mouse β-actin probe (Stratagene, La Jolla, Calif.). A PhosphoImager (Molecular Devices, Menlo Park, Calif.) is used to quantitate the amount of probe bound to the membrane.

i) Calcium mobilization response in CPR-expressing human CD8+ T cells

The mobilization of intracellular [Ca$^{2+}$] by CPR-expressing human CD8+ T cells is measured using Indo-1 acetomethoxyester (Molecular Probes, Eugene, Oreg.) on a FACStar Plus (Beckton Dickinson). Cells are collected by centrifugation, resuspended at 3×10$^6$/ml in complete medium containing 1 mM Indo-1 (Grynkiewicz et al., (1985) *J. Biol. Chem.* 260:3440–3450) and incubated at 37° C. for 45 min. The Indo-1-loaded cells are pelleted and resuspended at 1×10$^6$/ml in serum-free medium. Cells are then stimulated by treatment with either saturating levels of OKT4A or anti-human Fc Mab and cross-linking goat anti-mouse IgG, gp120, gp160-expressing cells, HIV-1 infected cells or FK1012, and fluorescence is measured. Maximal fluorescence is determined after lysis of cells with Triton X-100; minimal fluorescence is obtained after chelation of Ca$^{2+}$ with EGTA. Intracellular [Ca$^{2+}$] is determined using the following equation: $[Ca^{2+}]=K_d(F_{observed}-F_{min})/(F_{max}-F_{observed})$, with $K_d$=250 nM as described (Grynkiewicz, 1985).

j) Cytolytic activity of CPR-expressing human CD8+ T cells

To determine the cytolytic activity of CPR-expressing human CD8+ T cells, in vitro cytolytic assays are carried out with target cells expressing HIV-1 antigens. Gp160-expressing 293 cells or HIV-1 infected human T cells are labeled at 37° C. overnight with 10μCi [$^3$H]TdR (Roberts et al., *Blood* 84:2878–2889 (1994)), washed and aliquoted to 96-well V-bottom plates at 1×10$^4$/well. Serial dilutions of CPR-expressing human CD8+ T cells are made to achieve an effector to target (E:T) ratio ranging from 100:1 to 0.1:1. Sample are set up in triplicate and incubations are carried out for 6 hours at 37° C. Following incubation, aliquots of the culture supernatant are removed and counted in a liquid scintillation counter. Spontaneous release (SR) is obtained in a negative control sample lacking CPR-expressing human CD8+ T cells; maximum release (MR) is obtained from a positive control sample by lysing target cells with 1N HCl. The percent specific lysis is calculated from the following equation:

$$\% \text{ specific lysis}=(SR_{cpm}-Sample_{cpm})/(Sample_{cpm}-MR_{cpm})\times 100\%.$$

All publications, patents, and patent applications mentioned in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A method of inducing a cell to proliferate comprising:
   (a) introducing a proliferation receptor construct into said cell under conditions suitable for expression to produce a cell expressing a proliferation receptor protein; and
   (b) contacting said receptor in said cell with an inducer, said construct comprising in reading frame:
      a DNA sequence encoding an intracellular inducer-responsive clustering domain comprising an immunophilin or a cyclophilin; and
      a DNA sequence encoding a proliferation signaling domain comprising a Janus tyrosine kinase.

2. The method of claim 1 wherein said cell is selected from the group consisting of a nerve cell, a keratinocyte cell, islet of Langerhans cell, a muscle cell, or a hematopoietic cell.

3. A method of inducing a cell to proliferate comprising:
   (a) introducing a proliferation receptor construct into said cell under conditions suitable for expression to produce a cell expressing a proliferation receptor protein; and
   (b) contacting said receptor in said cell with an inducer, said construct comprising in reading frame:
      a DNA sequence encoding a signal sequence;
      a DNA sequence encoding an extracellular inducer-responsive clustering domain that binds specifically to at least one inducer molecule which results in the dimerization or oligomerization of said extracellular domain;
      a DNA sequence encoding a transmembrane domain; and
      a DNA sequence encoding a proliferation signaling domain comprising a Janus tyrosine kinase.

4. The method of claim 3, wherein said extracellular domain is an antibody, a single chain antibody or an antigen binding fragment of said antibody.

5. The method of claim 4, wherein said extracellular domain is CD8 or CD4.

* * * * *

UNITED STATES PATENT AND TRADEMARK OFFICE
CERTIFICATE OF CORRECTION

PATENT NO. : 5,837,544
DATED : November 17, 1998
INVENTOR(S) : Daniel J. Capon, Huan Tian, Douglas H. Smith, Genine A. Winslow and Miriram Siekevitz It is certified that error appears in the above-identified patent and that said Letters Patent is hereby corrected as shown below:

Claim 5, line 1, delete "claim 4" and insert --claim 3--.

Signed and Sealed this

Twentieth Day of July, 1999

Q. TODD DICKINSON

Attest:

Attesting Officer

Acting Commissioner of Patents and Trademarks